(12) United States Patent
Hsing et al.

(10) Patent No.: US 8,975,025 B2
(45) Date of Patent: Mar. 10, 2015

(54) METHOD AND SYSTEM FOR NUCLEIC ACID DETECTION USING ELECTROCONDUCTIVE OR ELECTROCHEMICALLY ACTIVE LABELS

(75) Inventors: I Ming Hsing, Hong Kong (HK); Ming Hung Thomas Lee, Hong Kong (HK); Xiaoteng Luo, Hong Kong (HK)

(73) Assignee: The Hong Kong University of Science and Technology, Hong Kong (CN)

( * ) Notice: Subject to any disclaimer, the term of this patent is extended or adjusted under 35 U.S.C. 154(b) by 926 days.

(21) Appl. No.: 13/169,055

(22) Filed: Jun. 27, 2011

(65) Prior Publication Data

US 2012/0058472 A1  Mar. 8, 2012

Related U.S. Application Data

(63) Continuation-in-part of application No. 12/377,124, filed as application No. PCT/CN2007/002395 on Aug. 10, 2007, now Pat. No. 8,465,926.

(60) Provisional application No. 60/836,990, filed on Aug. 11, 2006.

(51) Int. Cl.
*C12Q 1/68* (2006.01)
*C12P 19/34* (2006.01)

(52) U.S. Cl.
CPC .................................... *C12Q 1/6825* (2013.01)
USPC .................. 435/6.11; 435/6.12; 435/91.2

(58) Field of Classification Search
USPC ....................................... 435/6.11, 6.12, 91.2
See application file for complete search history.

(56) References Cited

U.S. PATENT DOCUMENTS

2004/0110214 A1*  6/2004  Kim et al. .......................... 435/6
2006/0228703 A1*  10/2006  Hartwich et al. ................ 435/6

OTHER PUBLICATIONS

Xiaoteng Luo, I-Ming Hsing, Immobilization-free multiplex electrochemical DNA and SNP detection, Biosensors and Bioelectronics 25 (2009) 803-808, Elsevier B.V.
Xiaoteng Luo, I-Ming Hsing, Sequence Specific Electrochemical DNA Detection Based on Solution-Phase Competitive Hybridization, Electroanalysis 2010, 22, No. 23, 2769-2775, Wiley-VCH Verlag GmbH & Co. Weinheim.
Xiaoteng Luo, Thomas Ming-Hung Lee, and I-Ming Hsing Immobilization-Free Sequence-Specific Electrochemical Detection of DNA Using Ferrocene-Labeled Peptide Nucleic Acid, Analytical Chemistry, 2008, 80 (19), 7341-7346, American Chemical Society, Washington, DC 20036.
V. A. T. Dam, W. Olthuis and A. Van Den Berg, Redox cycling with facing interdigitated array electrodes as a method for selective detection of redox species, Analyst, 2007, 132, 365-370, The Royal Society of Chemistry.

(Continued)

*Primary Examiner* — Kenneth Horlick
(74) *Attorney, Agent, or Firm* — Eagle IP Limited; Jacqueline C. Lui

(57) ABSTRACT

A method for electrochemically or electrically detecting nucleic acids, utilizes electrochemically active or electrically conductive reporter materials. An electric voltage is applied and electric signals are measured to the electrodes that are suitable for detecting or quantifying the nucleic acid(s) in a sample. This technique is suitable for point-of-use applications, e.g. detecting bioanalytes in remote locations. A microchip, device, kit used adapted to be used for this method is also disclosed.

14 Claims, 18 Drawing Sheets

(56) References Cited

OTHER PUBLICATIONS

Allen J. Bard, Joseph A. Crayston, Gregg P. Kittlesen, Theresa Varco Shea, and Mark S. Wrighton, Digital Simulation of the Measured Electrochemical Response of Reversible Redox Couples at Microelectrode Arrays: Consequences Arising from Closely Spaced Ultramicroelectrodes, Analytical Chemistry, vol. 58, No. 11, 1986, 2321-2331.

Minhaz Uddin Ahmed, Koutarou Idegami, Miyuki Chikae, Kagan Kerman, Piyasak Chaumpluk, Shonei Yamamura and Eiichi Tamiya, Electrochemical DNA biosensor using a disposable electrochemical printed (DEP) chip for the detection of SNPs from unpurified PCR amplicons, Analyst, 2007, 132, 431-438, The Royal Society of Chemistry.

Masaaki Kobayashi, Takashi Kusakawa, Masato Saito, Sakiko Kaji, Miyuki Oomura, Shinichiro Iwabuchi, Yasutaka Morita, Quamrul Hasan and Eiichi Tamiya, Electrochemical DNA quantification based on aggregation induced by Hoechst 33258, Electrochemistry Communications 6 (2004) 337-343, Elsevier B.V.

Teh Huey Fanga, Naveen Ramalingama, Dong Xian-Duib, Tan Swee Nginc, Zeng Xiantingd, Annie Tan Lai Kuand, Eric Yap Peng Huate and Gong Hai-Qing, Real-time PCR microfluidic devices with concurrent electrochemical detection, Biosensors and Bioelectronics 24 (2009) 2131-2136, Elsevier B.V.

Heiko Duwensee, Martin Jacobsen and Gerd-Uwe Flechsig, Electrochemical competitive hybridization assay for DNA detection using osmium tetroxide-labelled signalling strands, Analyst, 2009, 134, 899-903, The Royal Society of Chemistry.

Kyuwon Kim, Haesik Yang, Se Ho Park, Dae-Sik Lee, Sung-Jin Kim, Yong Taik Lim and Youn Tae Kim, Washing-free electrochemical DNA detection using double-stranded probes and competitive hybridization reaction, Chemical Communication, 2004, 1466-1467, The Royal Society of Chemistry, Cambridge, UK.

P. Liepold, T. Kratzmüller, N. Persike, M. Bandilla, M. Hinz, H. Wieder, H. Hillebrandt, E. Ferrer and G. Hartwich, Electrically detected displacement assay (EDDA): a practical approach to nucleic acid testing in clinical or medical diagnosis, Anal Bioanal Chem (2008) 391:1759-1772, Springer-Verlag.

Mónica Mir, Pablo Lozano-Sánchez and Ioanis Katakis, Towards a target label-free suboptimum oligonucleotide displacement-based detection system, Anal Bioanal Chem (2008) 391:2145-2152, Springer-Verlag.

\* cited by examiner

METHOD AND SYSTEM FOR NUCLEIC ACID DETECTION USING ELECTROCONDUCTIVE OR ELECTROCHEMICALLY ACTIVE LABELS

CROSS-REFERENCE TO RELATED APPLICATION

This application is a continuation-in-part of U.S. Ser. No. 12/377,124 filed 11 Feb. 2009 under 35 U.S.C. §371(c)(1), (2), (4) which is a US national phase application of PCT international application No. PCT/CN07/02395 filed 10 Aug. 2007, in which the PCT international application claims benefit under 35 U.S.C. §119(e) of U.S. Provisional Application having Ser. No. 60/836,990 filed 11 Aug. 2006, which is hereby incorporated by reference herein in its entirety.

REFERENCE TO SEQUENCE LISTING

The hard copy of the sequence listing submitted herewith and the corresponding computer readable form are both incorporated herein by reference in their entireties.

FIELD OF THE INVENTION

The present invention relates to a novel and unobvious method for detecting and quantifying nucleic acids and nucleic acid-coupled molecules, where the electrochemical or electrically conductive label attaches itself to the target nucleic acid.

DESCRIPTION OF THE BACKGROUND

Nucleic acid analysis has played an important role for the detection of pathogens and genetic diseases. In recent years, its usefulness has been seen in many decentralized applications such as point-of-care diagnostics, environmental and food monitoring, and the detection of biological warfare agents.

In a typical electrochemical DNA detection scheme, one of the essential steps is to immobilize a DNA or PNA (peptide nucleic acid) probe on the surface of a substrate (usually the detecting electrode). In cooperation with some washing steps, the immobilization of the DNA or PNA probe enables separation and differentiation of the target DNA which hybridizes with the immobilized probe from the non-target DNAs which do not hybridize with the probe. However, problems with these "immobilization-based" electrochemical DNA detection methods arise including that the bonding strength of the surface-linked DNA might not survive the high temperature cycling during polymerase chain reaction (PCR). Furthermore, for immobilization-based electrochemical DNA detection schemes, multiplexing would be a huge challenge, as it would add a lot to complexity of the assay and the accuracy of detection may be affected by interference between the detection of different targets.

The inventors have previously developed an "immobilization-free" electrochemical DNA detection approach and disclosed in Luo, X., et al. (Anal. Chem. 2008). This approach uses ferrocene-labeled PNA based on the neutral PNA backbone and the electrostatic interaction between the negative DNA backbone and the negative electrode surface. The inventors have also showed the success in using this approach for multiplexed DNA detection and disclosed in Luo X., et al. (Biosens. and Bioelectron. 2009). Apart from the detection strategy discussed above, other electrochemical DNA detection schemes that require no probe immobilization with "sig-nal-off" operation have also been studied and reported by other groups. For instance, Tamiya et al. reported in their papers (Ahmed M. U., et al., Analyst 2007; Kobayashi M., et al., Electrochem. Commun. 2004) such an immobilization-free DNA detection method based on the reduced diffusion coefficient of intercalated Hoechst 33258 leading to a reduced electrochemical signal in the presence of double stranded DNA. A similar strategy has also been developed by Gong's group, using methylene blue for the real-time electrochemical monitoring of PCR amplicons as disclosed in Fang T. H., et al. (Biosens. and Bioelectron. 2009).

In addition, the principle of "competitive hybridization" has been utilized for electrochemical DNA detection in a number of reports, such as Duwensee H., et al. (Analyst 2009), Kim K., et al. (Chem. Commun. 2004), Liepold P., et al. (Anal. Bioanal. Chem. 2008), and Mir M., et al. (Anal. Bioanal. Chem. 2008). All these detection schemes have one characteristic in common, which is that the competitive hybridization occurs at the interface between a solution and an electrode surface. As the DNA probe is immobilized on the electrode, the target DNA and the competitor DNA has to diffuse to the electrode surface in order to hybridize with the probe, which results in low hybridization efficiency and therefore, long assay time.

Among the available analytical techniques for DNA analyses, real-time polymerase chain reaction has been a key technology for high-speed testing and accurate quantification.

Various assays based on real-time PCR have been developed utilizing fluorescence-linked reporters such as SYBR Green 1, hydrolysis probe, and hybridization probes for simultaneous deoxyribonucleic acid (DNA) amplification and PCR amplicon detection. Despite wide acceptance, their use is largely limited in clinical and research laboratory settings. The difficulty in advancing this technology for point-of-care testing (POCT) applications lies in the requirement of bulky and complex optical systems for the DNA amplicon detection. The goal of performing complete DNA analyses with a hand-held instrument is not attainable based on optical detection systems that are bulky and cumbersome. A far more suitable alternative for this type of use and one that is extremely suited for POCT, is a system based on the detection of electrochemical signals.

Over the past years, numerous studies have been carried out on electrochemical DNA sensors, some of which focused on PCR amplicon detection. Efforts have also been made in developing DNA microchips having an attached electrochemical signaling label employed in conjunction with an electrochemical detection system for post-PCR product identification. The latter prior art post-PCR hybridization-based platform suffers from a long assay time and has a narrow dynamic range when compared to fluorescence-based real-time PCR methods.

In view thereof, there is a need for developing a method for detecting and quantifying nucleic acid(s) in a sample that is accurate, reproducible, and safe and, at the same time, may be performed in small scale devices.

SUMMARY OF THE INVENTION

In light of the foregoing background, it is an object of the present invention to provide a method for the detection and quantification of nucleic acid(s) or nucleic acid coupled molecules in a sample and a system thereof.

Accordingly, the present invention, in one aspect, is a real time solid phase method for electrochemically or electrically monitoring or quantifying the amount of nucleic acid(s) by formation of a polymerase chain reaction (PCR) produced polynucleic acid(s), that comprises the following steps:

contacting a sample comprising a target nucleic acid(s), a solid surface bound probe(s) comprising a first primer(s) provided with a sequence(s) that is(are) complementary to at least a portion of one end of the target nucleic acid(s), a second primer(s) in solution that is(are) complementary to at least a portion of the opposing end of the complementary strand of the target nucleic acid(s), and an electrochemically or electrically conductive marker(s) that is(are) adapted for incorporation into a polynucleic acid(s) by chain polymerization and when incorporated thereof produces a signal(s) change(s) if subjected to an electric potential;

adding a polymerase chain reaction enzyme(s) under conditions effective for PCR amplification to occur;

applying an electric potential to the sample and detecting or measuring in real time the electric signal(s) produced by the labeled marker(s) incorporated into the solid surface bound probes; and quantifying the amount of nucleic acid(s) present in the sample and the amount of polynucleic acid(s) produced by correlating the change(s) in signal(s) over time with the formation of polynucleic acid(s).

In a further aspect of the present invention, a solution phase method for electrochemically or electrically detecting target nucleic acid(s) is provided, which comprises the steps of:

a). providing a sample comprising a first probe(s) having the same electrical polarity as that of an electrode surface such that said first probe(s) is(are) repelled from said electrode surface; and a second probe(s) comprising an electrochemically or electrically conductive labeled marker(s) coupled to an electrically neutral molecule(s), the second probe being operatively linked to said first probe(s);

b). providing the target nucleic acid(s) to the sample wherein the first probe(s) is(are) complementary to at least a portion of the target nucleic acid(s); and c). applying an electric potential to the sample and detecting or measuring a signal(s) produced by the labeled marker(s)

wherein when the first probe(s) is(are) hybridized into the target nucleic acid(s), the second probe(s) is(are) released from the first probe(s) and the labeled marker(s) is(are) freely diffused to the electrode surface to produce a signal intensity change(s) when subjected to an electric potential.

In a further aspect of the present invention a solution phase method for electrochemically or electrically detecting target nucleic acid(s) is provided in which the target nucleic acid(s) is(are) produced in a polymerase chain reaction (PCR); the method further comprises the step of quantifying the amount of said target nucleic acid(s) produced by correlating the change(s) in signal(s) over time with the formation of said target nucleic acid(s).

In yet a further aspect of the present invention, a microchip is provided, and comprises an electrochemically or electrically conductive electrode(s) provided on a surface adapted to receive a molecule comprising a nucleic acid(s) wherein the microchip is adapted to be used for the solid phase or solution phase method as described above. In a preferred embodiment, the surface comprises a solid support; in a more preferred embodiment, the solid support comprises glass, and the electrode surface is made of a material selected from a group consisting of indium tin oxide, gold, platinum and carbon materials. and is(are) patterned and integrated into said microchip. In yet another preferred embodiment, the electrode(s) comprise(s) interdigitated array electrode(s).

In another preferred embodiment, the microchip further comprises a temperature sensor(s) and a micro heater(s) integrated therein. In one preferred embodiment, the temperature sensor comprises a metal selected from platinum, gold, and copper.

Yet another aspect of the present invention provides a device for measuring electrochemical or electric signals, comprising the microchip of this invention. In a preferred embodiment, the device is a portable device and/or a microdevice.

In another aspect of the present invention, an electrochemical signal detection kit is provided comprising a plurality of PCR primers and one or a plurality of the microchips of this invention; in a more preferred embodiment, the kit further comprises PCR reagents other than primers, and the like.

There are many advantages of the present invention. For instance, unlike the hybridization in immobilization-based DNA detections which occur on a solution-electrode interface as afore-discussed, the hybridization in the immobilization-free scheme of the instant invention occurs in a homogeneous solution phase and greatly reduces the assay time with a higher hybridization efficiency. Thus, the signal-on immobilization-free electrochemical DNA detection of the instant invention can produce more reliable results than the afore-mentioned signal-off method and have a good potential to be developed into a simple and robust electrochemical DNA detection for point-of-care testing. For example, it may be integrated into hand-held instruments for point-of-care DNA analysis. This provides a significant contribution to the medical diagnostics industry as well as to environmental monitoring for decentralized applications.

Further, the solution method of the instant invention operates in a "signal-on" mode in which the presence of target DNA results in the increment of the signal. Therefore, it is unlikely that any factor other than the presence of target DNA would lead to the appearance or enhancement of the specific electrochemical signal.

For the detection and/or quantification of nucleic acid amplification product is performed in real time during the PCR reaction, it is important to note that the method and system according to this invention are thermally stable, having a negligible inhibitory effect on the PCR reaction. Also, this method is accurate, reproducible, and safe, even in the absence of an additional step of washing off of unreacted molecules, especially the soluble and non-incorporated labeled molecules and markers employed in the reaction.

When compared to optically-based devices, the present invention provides a technology that results in significantly reduced expenses; more particularly, this method may be employed in miniaturized devices, e.g. a portable real time PCR analyzer, which is currently unavailable in the market place.

and (C) the final extended capture probe at the end of the PCR according to one embodiment of the present invention.

Figure 4:
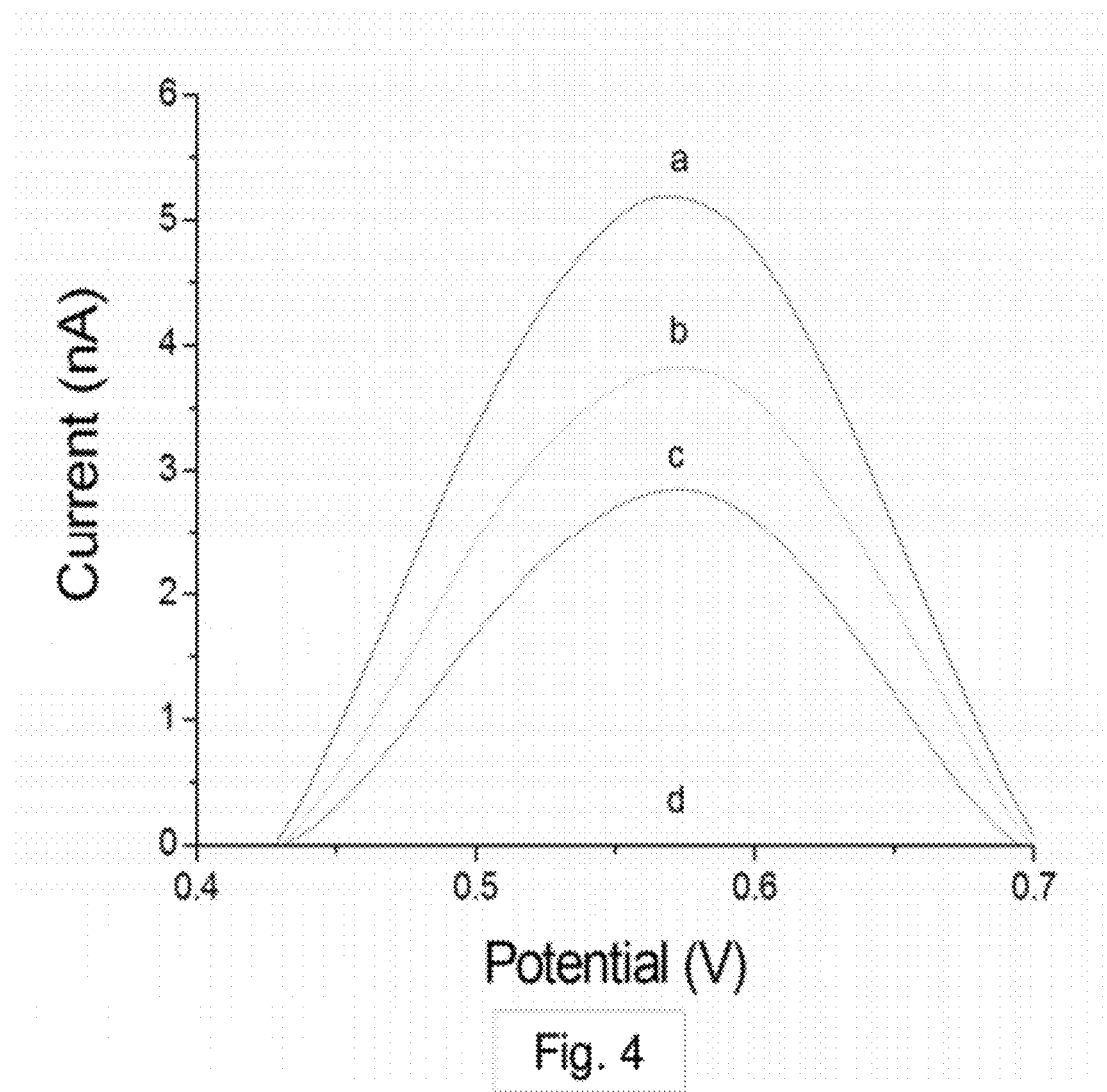

FIG. 4 is a differential pulse voltammetric scan of the ITO electrodes in the absence of the template according to the same embodiment of the present invention. The chips were incubated with ethanolamine for different times: (a) 1 hour; (b) 2 hours; (c) 3 hours; and (d) 12 hours. Electrochemical measurements were carried out using a pulse amplitude of 100 mV/s and a scan rate of 25 mV/s. The background signals were obtained at the end of 30-cycle PCRs.

Figure 5A:
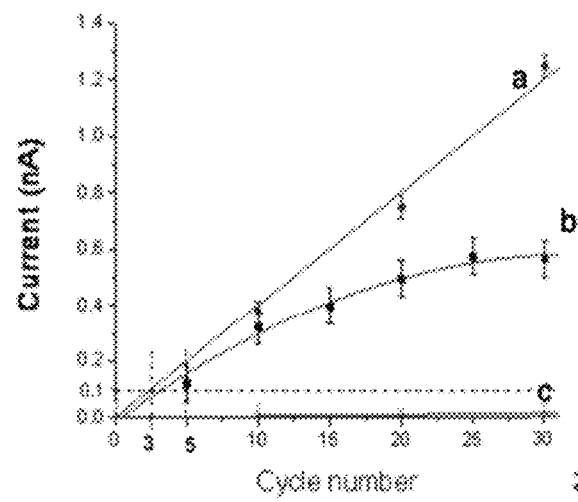

FIG. 5A shows a plot of peak current signal in a differential pulse voltammetric scans against PCR cycle number with different electrode scanning strategies according to the same embodiment of the present invention. (a) ● Single-scan in the presence of template ($3\times10^6$ copies/µL); (b) ■ multiple-scan in the presence of template ($3\times10^6$ copies/µL); and (c) ▲ single-scan in the absence of template.

Figure 5B:
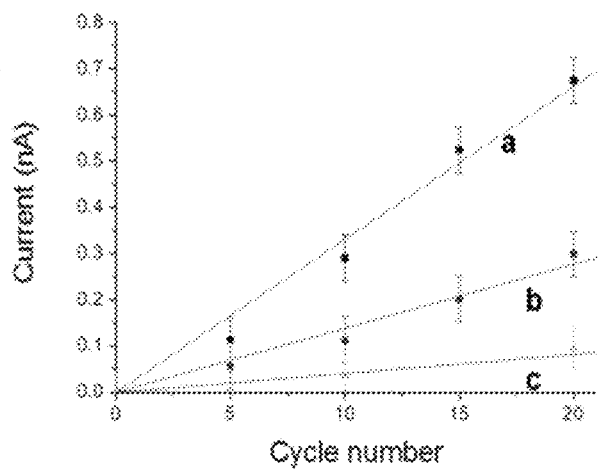

FIG. 5B shows a plot of current signal against PCR cycle number in the presence of target DNA template ($3\times10^3$ copies/µL) at different Vent polymerase concentrations according to one embodiment of the present invention. (a) ■ 0.32 units/µL; (b) ● 0.24 units/µL; and (c) ▲ 0.04 units/uL.

Figure 5C:
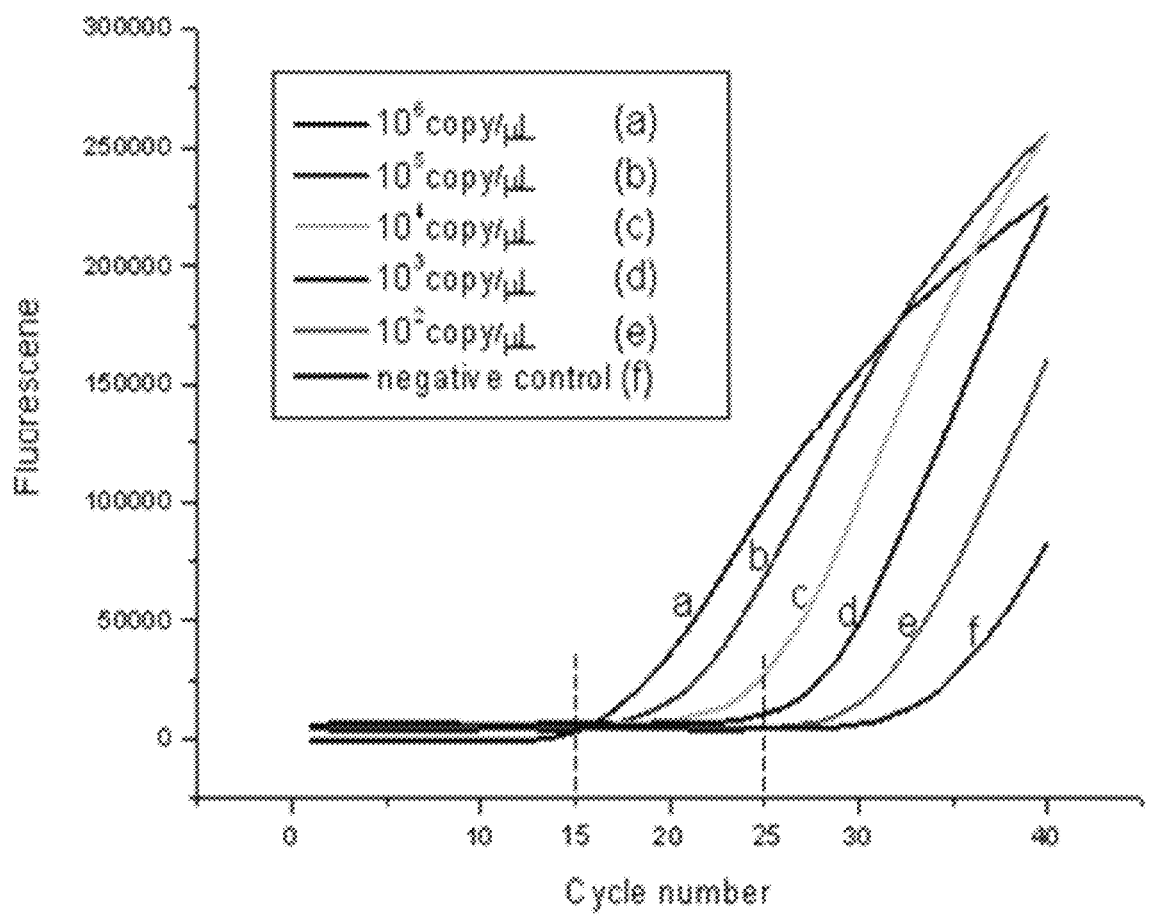

FIG. 5C shows a plot of fluorescent signal (SYBR Green assay) against PCR cycle number for a series of dilutions from $10^2$ to $10^6$ DNA copies/µL. (a) $10^6$ copy/µL; (b) $10^5$ copy/µL; (c) $10^4$ copy/µL; (d) $10^3$ copy/µL; (e) $10^2$ copy/µL; (f) negative control.

Figure 6A:
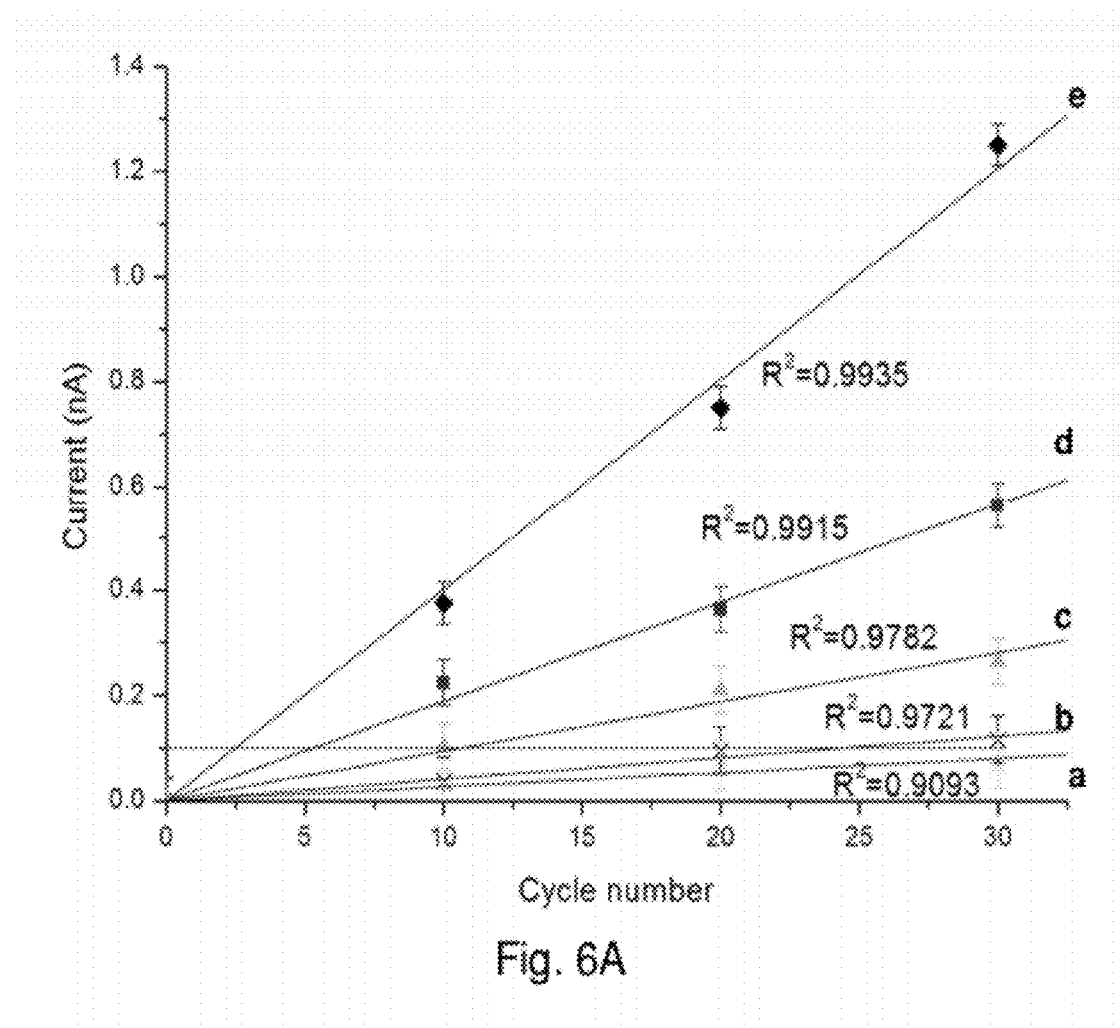
Figure 6B:
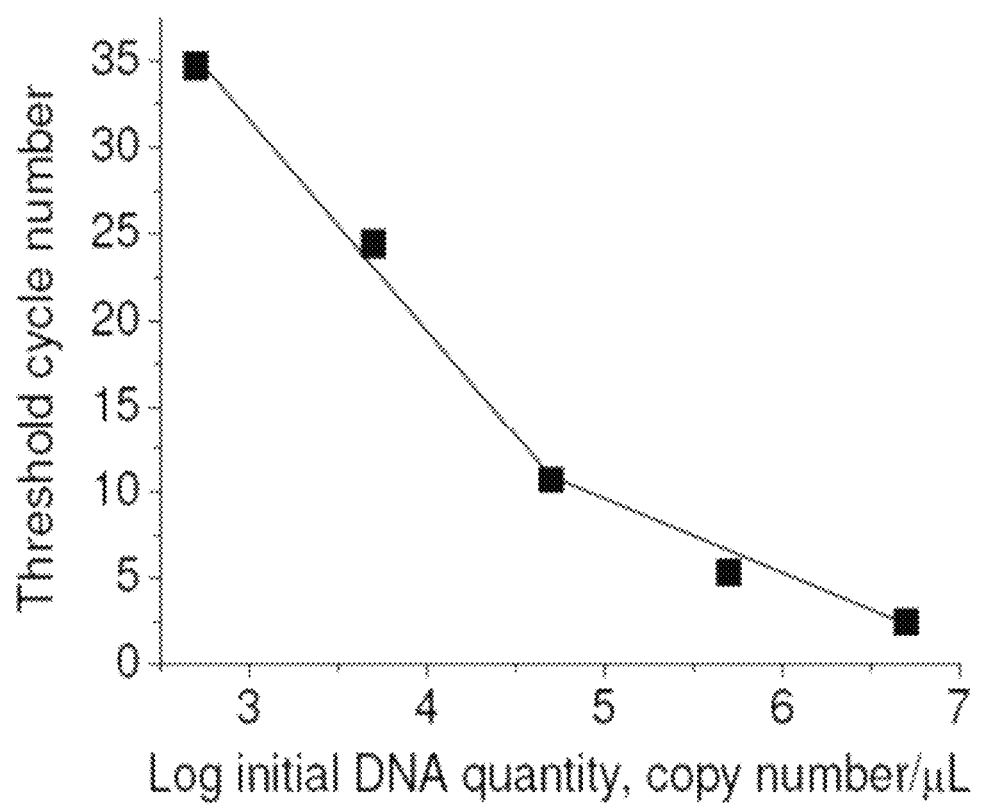

FIG. 6A shows a plot of peak current signal against PCR cycle number for a series of dilutions from $10^2$ to $10^6$ DNA copies/µL. (a) * $3\times10^2$; (b) x $3\times10^3$; (c) ▲ $3\times10^4$; (d) ■ $3\times10^5$; (e) ◆ $3\times10^6$ according to one embodiment of the present invention. FIG. 6B is a standard curve with a threshold set at 0.1 nA according to the same embodiment.

Figure 7:
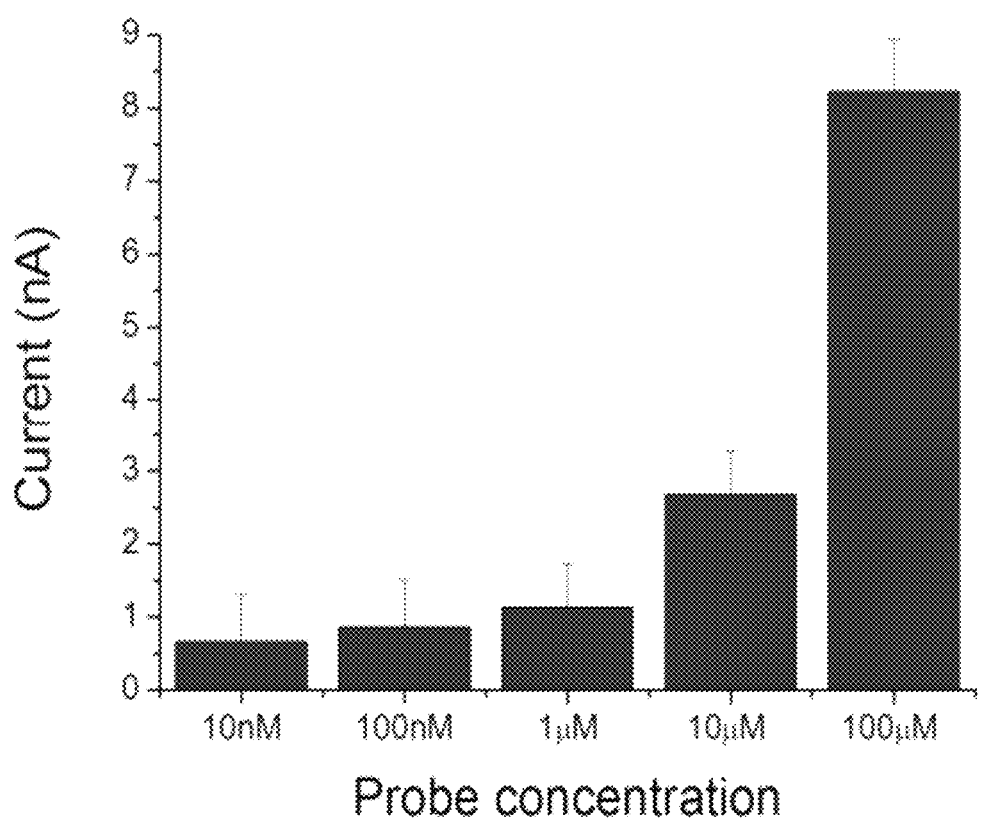

FIG. 7 shows a plot of peak current signal after 30-cycle PCR against probe concentration according to one embodiment of the present invention. The probe concentration ranges from 10 nM to 100 µM in the probe immobilization step, with the initial template concentration being $3\times10^6$ copies/µL.

Figure 8:
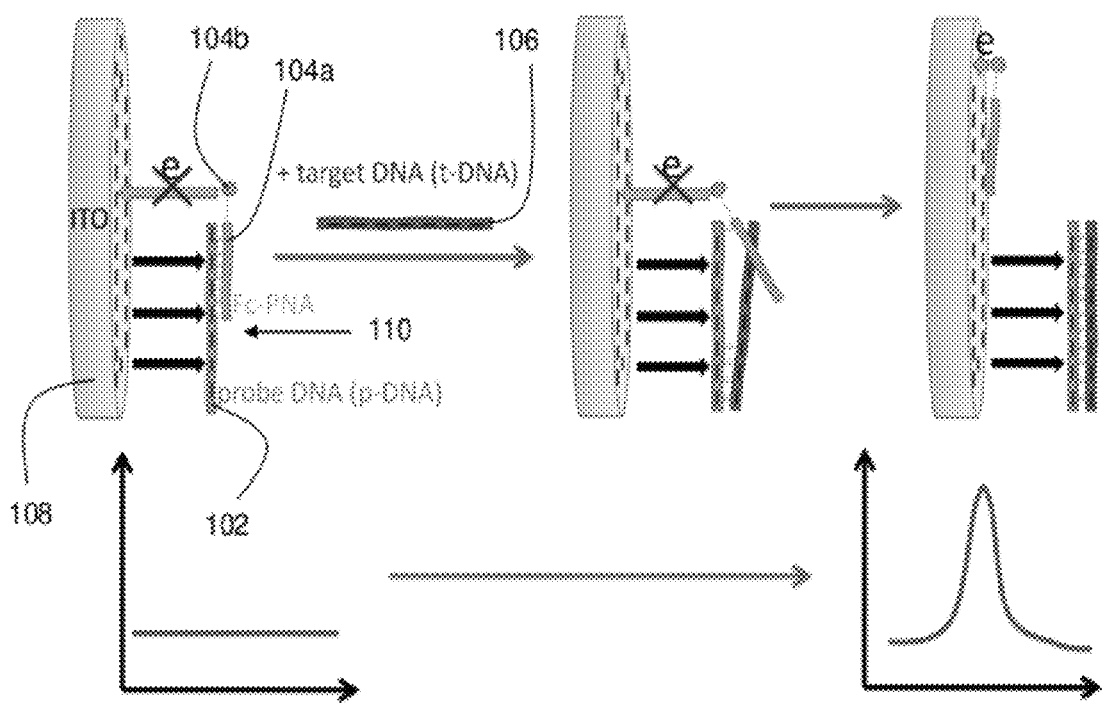

FIG. 8 is an illustration showing the principle of signal-on immobilization-free electrochemical DNA detection according to one embodiment of the instant invention.

Figure 9A:
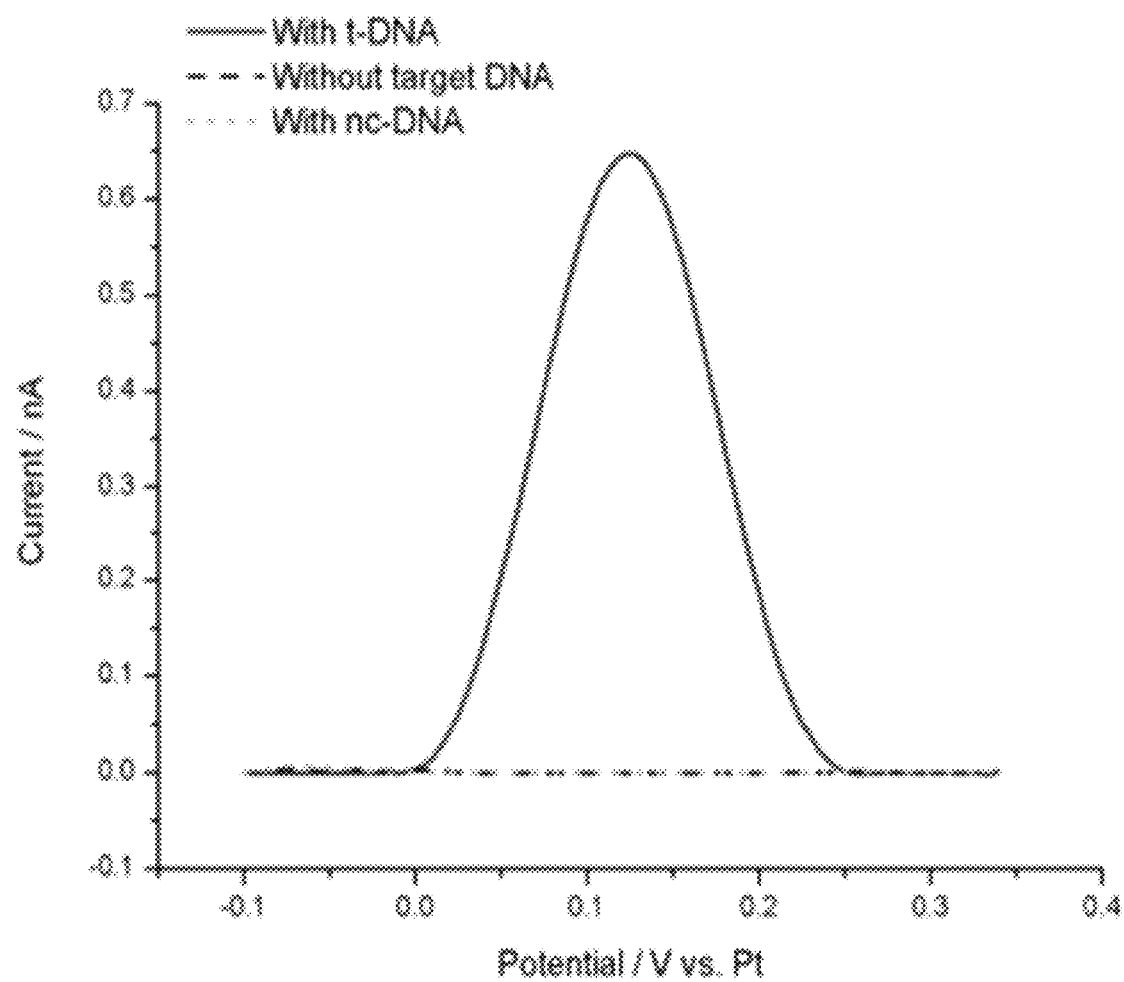

FIG. 9A shows a differential pulse voltammograms (DPVs) of 1 µM Fc-PNA mixed with 2 µM t-DNA and 2 µM p-DNA (—), 1 µM Fc-PNA mixed with 2 µM p-DNA only (- - - -), and 1 µM Fc-PNA mixed with 2 µM nc-DNA and 2 µM p-DNA (. . . . . .) according to the same embodiment of the instant invention. DPVs were carried out on ITO electrode using a pulse amplitude of 100 mV/s and a scan rate of 25 mV/s.

Figure 9B:
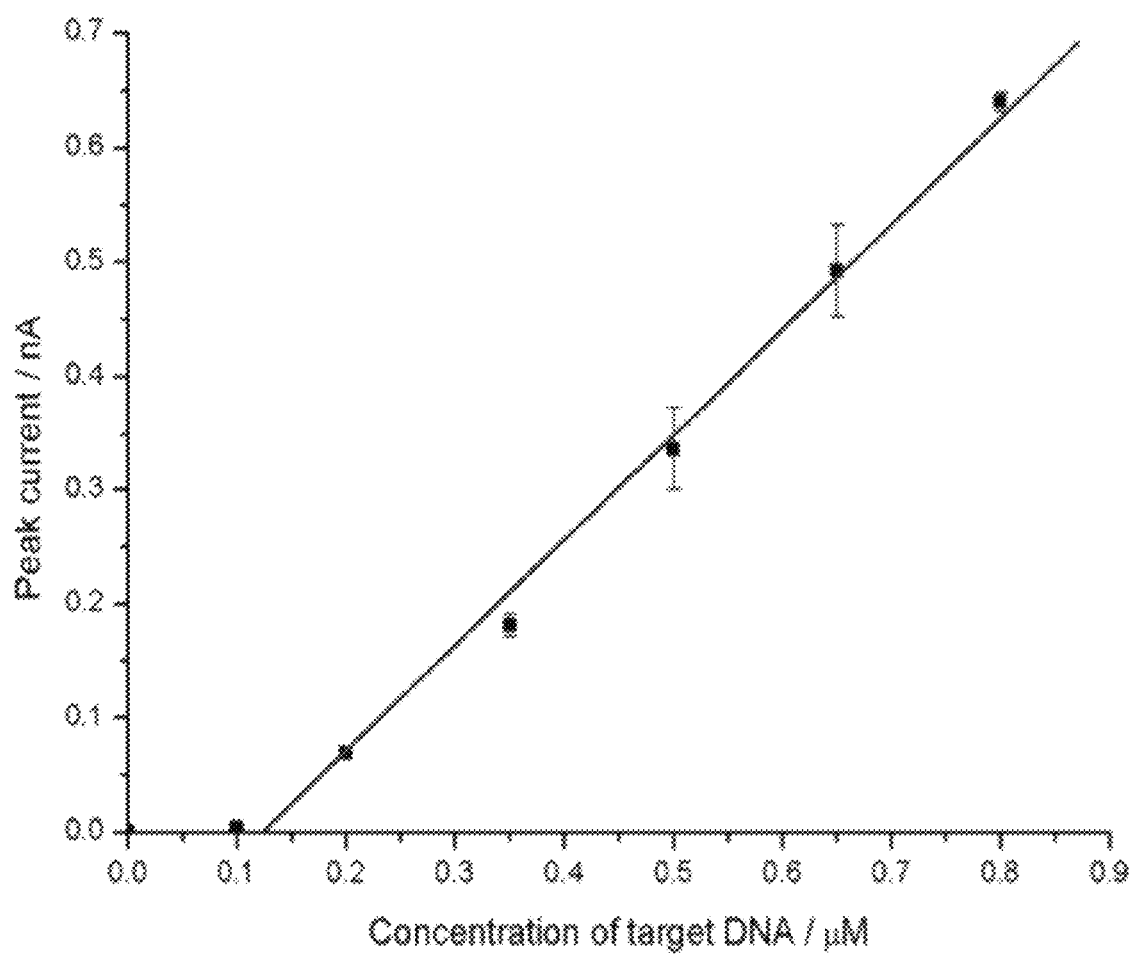

FIG. 9B shows a Plot of peak current signal in differential pulse voltammetric scans against concentration of t-DNA according to the same embodiment of the instant invention.

Figure 10A:
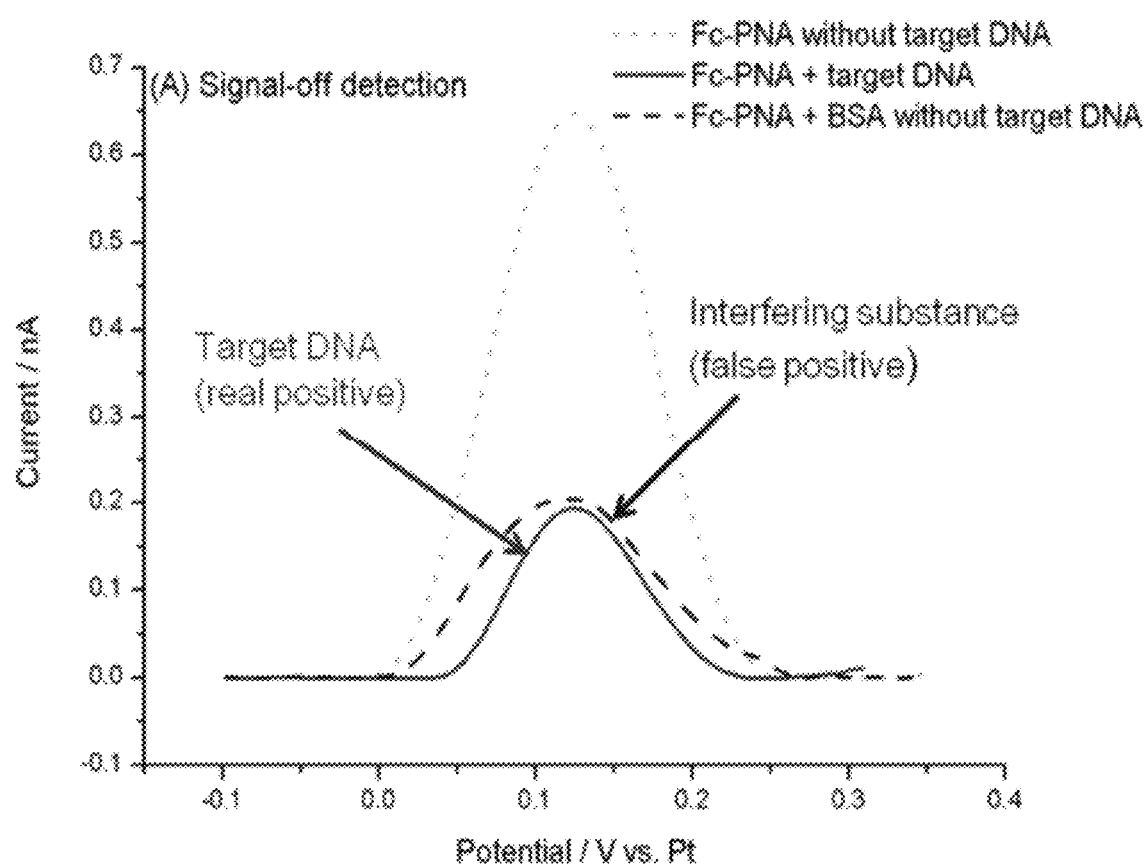

FIG. 10A shows a differential pulse voltammograms of 1 µM Fc-PNA only (. . . . . .), 1 µM Fc-PNA mixed with 0.8 µM of p-DNA (—), 1 µM Fc-PNA mixed with 1 µg/µL BSA (- - - -) according to the same embodiment of the instant invention.

Figure 10B:
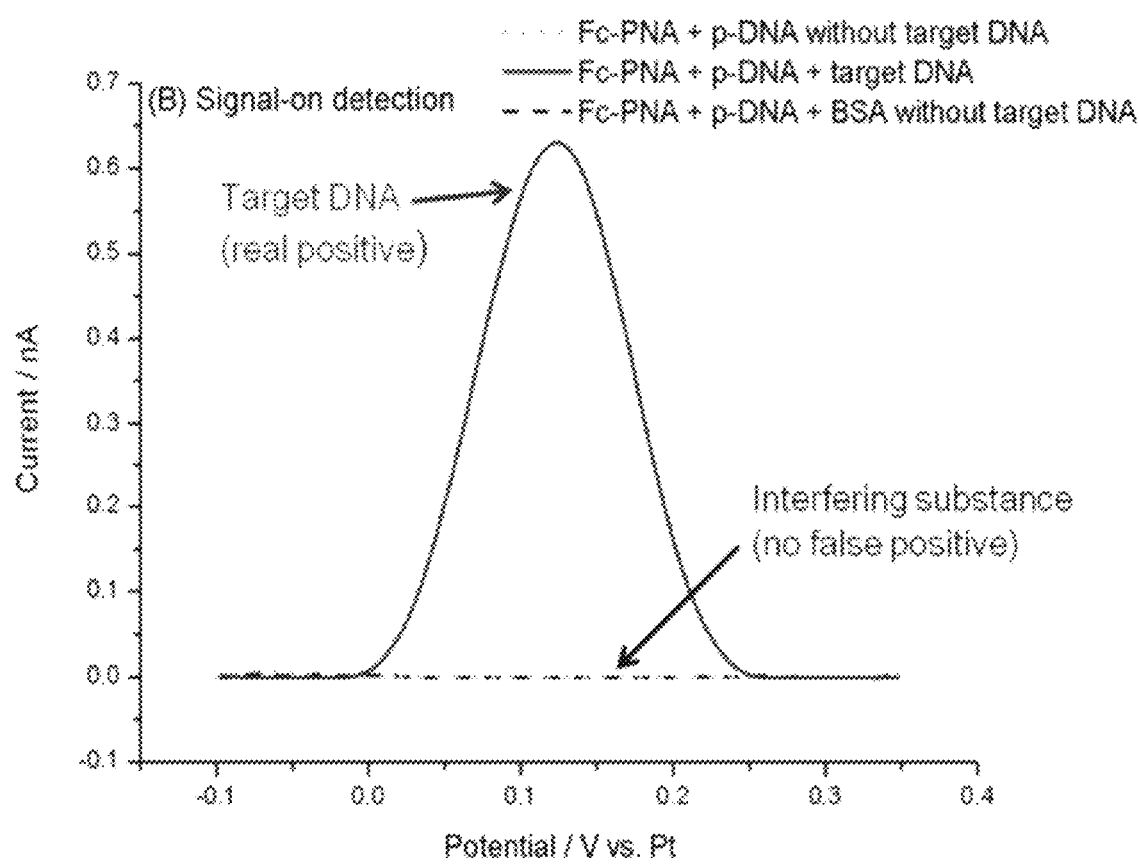

FIG. 10B shows a differential pulse voltammograms of 1 µM Fc-PNA mixed with 1 µM of p-DNA (. . . . . .), 1 µM Fc-PNA mixed with 1 µM of p-DNA and 0.8 µM of t-DNA (—), 1 µM Fc-PNA mixed with 1 µM of p-DNA and 1 µg/µL BSA (- - - -) according to the same embodiment of the instant invention.

Figure 11A:
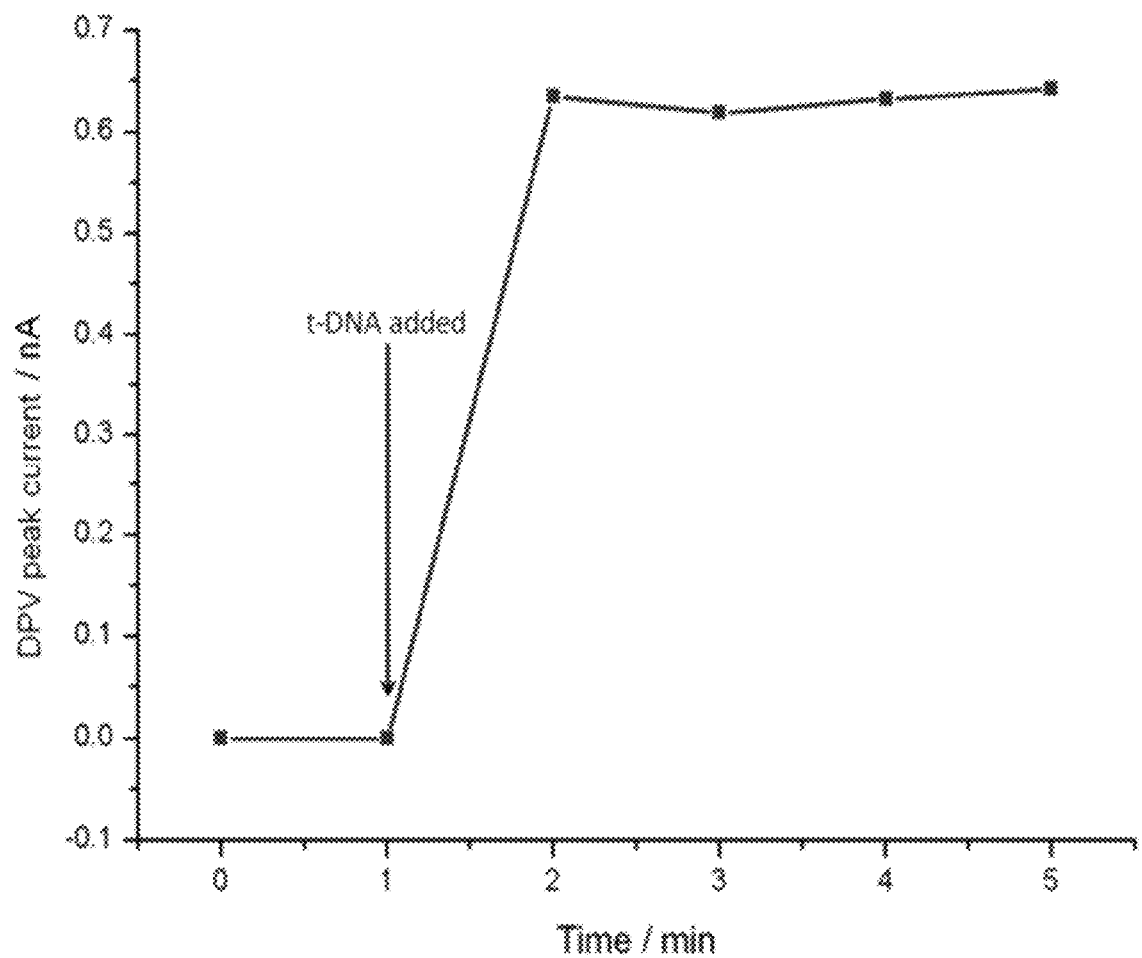

FIG. 11A shows a peak current intensity in differential pulse voltammetric scans of 1 µM Fc-PNA mixed with 2 µM p-DNA plotted against time. 2 µM t-DNA was added at the 2nd minute according to the same embodiment of the instant invention.

Figure 11B:
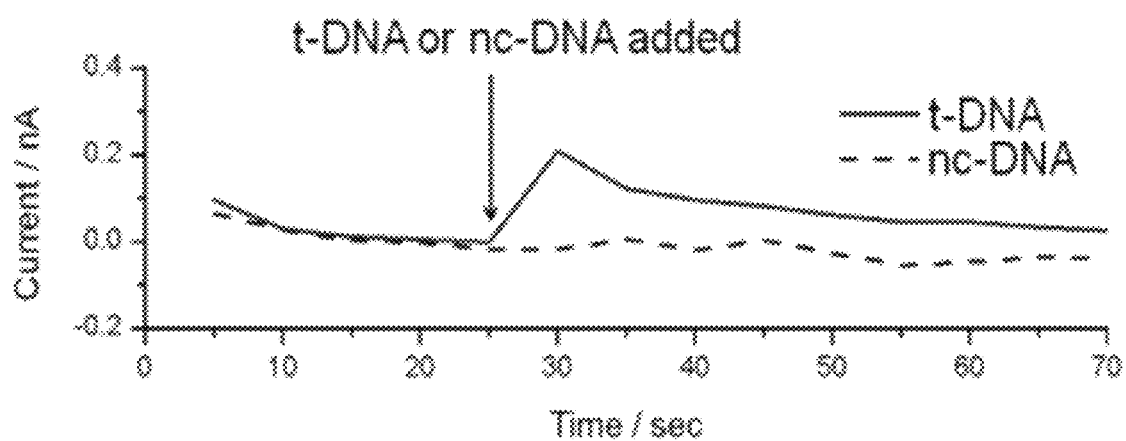

FIG. 11B shows a chronoamperometry of 1 µM Fc-PNA mixed with 2 µM p-DNA, with 2 µM t-DNA (—) or 2 µM nc-DNA (- - - -) added at the 25th second according to the same embodiment of the instant invention.

DETAILED DESCRIPTION OF THE PREFERRED EMBODIMENTS

This invention arose from the desire by the inventors to improve on prior art technology and, at the same time, overcome the cumbersome and expensive type of hardware that are currently required in the art. This invention aims to address the deficiencies inherent in the currently employed optically, e.g. fluorescence-based PCR methods that are standard in the industry, and is an improvement over the real time detection method employing an electrochemical label attached to the solid substrate.

During the course of their investigations, the inventors endeavored to discover a simpler, less expensive, and generally superior device and method for detection and quantification of nucleic acids. The inventors came into the realization that of many alternatives tested, the PCR reaction conditions were best suited for being coupled to a detection system based on electrochemical/electrical signals. Moreover, by coupling this detection method to a PCR reaction with appropriate electrochemical or electrically conductive reporter(s), amplicon(s) or probe(s), where the electrochemical label would be incorporated into the amplified nucleic acid, they would be able to provide a superior method of detection and quantification of target macromolecules, such as nucleic acids or nucleic acid coupled molecules, that is less costly, simpler and more accurate than prior art methods.

DEFINITIONS

As used herein and in the claims, a "sample" refers to a sample of tissue or fluid isolated from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components).

The terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. There is no intended distinction in length between the term "nucleic acid", "polynucleotide" and "oligonucleotide", and these terms will be used interchangeably. These terms refer only to the primary structure of the molecule. Thus, these terms include double- and single-stranded DNA, as well as double- and single stranded RNA. The oligonucleotide is comprised of a sequence of approximately at least 6 nucleotides, preferably at least about 10-12 nucleotides, and more preferably at least about 15-20 nucleotides corresponding to a region of the designated nucleotide sequence. "Corresponding" means identical to or complementary to the designated sequence.

The oligonucleotide is not necessarily physically derived from any existing or natural sequence but may be generated in any manner, including chemical synthesis, DNA replication, reverse transcription or a combination thereof. The terms "oligonucleotide" or "nucleic acid" intend a polynucleotide of genomic DNA or RNA, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature; and (3) is not found in nature.

The term "peptide nucleic acid (PNA)" refers to an artificially synthesized chemical having a structure resembling DNA or RNA, in which the backbone of PNA is composed of repeating N-(2-aminoethyl)-glycine units linked by peptide bonds such that various purine and pyrimidine bases can be linked to the backbone by methylene carbonyl bonds. By virtue of this structure, PNA is electrically neutral.

The term "primer" may refer to more than one primer and refers to an oligonucleotide, whether occurring naturally, as in a purified restriction digest, or produced synthetically, which is capable of acting as a point of initiation of synthesis along a complementary strand when placed under conditions in which synthesis of a primer extension product which is complementary to a nucleic acid strand is catalyzed. Such conditions include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

As used herein and in the claims, the term "target nucleic acid", "target sequence" or "target nucleic acid sequence" refers to a region of the oligonucleotide which is to be either amplified, detected or both. The target sequence resides between the two primer sequences used for amplification.

The term "probe" refers to a labeled oligonucleotide which forms a duplex structure with a sequence in the target nucleic acid, due to complementarity of at least one sequence in the probe with a sequence in the target region. Specifically for the solid phase method, once all the probes are attached onto the electrode surface, all the remaining active sites on the electrode surface may be "blocked" to restrict the incorporation of unbound or unreacted labeled markers into the electrode surface.

The term "label" as used herein and in the claims refers to any atom or molecule which can be used to provide a detectable (preferably quantifiable) signal, and which can be attached to a nucleic acid or protein.

By "adjacent" refers to the positioning of the primer with respect to the probe on its complementary strand of the template nucleic acid. The primer and probe may be separated by 1 to about 20 nucleotides, more preferably, about 1 to 10 nucleotides, or may directly abut one another, as may be desirable for detection with a polymerization-independent process. Alternatively, for use in PCR amplification and detection methods as taught herein, the "adjacency" may be anywhere within the sequence to be amplified.

As used herein and in the claims, "operatively linked", "bound" or "coupled", in a broad sense, refers to the association between molecules or a molecule and a substrate's surface and include, among others, either a direct or indirect (covalent or ionic) linking therebetween. For ease of description, the term "bound" is generally used to refer to the association between a molecule and a solid surface, whereas "coupled" generally refers to the association between two molecules. The phrase "operatively linked" includes all types of linkages, whether ionic or covalent, molecule to molecule or molecule to surface. The term "electrochemically or electrically conductive labeled markers", as used herein, refers to markers coupled to electrochemical or electrically conductive molecules.

The term "ferrocene derivatives" refer to chemical compounds having two cyclopentadienyl rings bound on opposite sides of a central metal atom, such as iron, in a sandwich structure.

The Invention

The practice of the present invention employs, unless otherwise indicated, conventional techniques of molecular biology, which are within the skill of the art. Such techniques are explained fully in the literature. See, e.g., Sambrook, Frtisch & Maniatis, Molecular Cloning; A Laboratory Manual, Second Edition (1989); Oligonucleotide Synthesis (M. J. Gait, ed., 1984); and Nucleic Acid Hybridization (B. D Hames & S. J. Higgins, eds., 1984). All patents, patent applications, and publications mentioned herein, both supra and infra, are hereby incorporated by reference.

The reagents employed in the methods of the invention may be packaged into diagnostic kits. Diagnostic kits include the labeled marker(s) and the primers in separate containers. If the marker is unlabeled, the specific labeling reagents may also be included in the kit. The kit may also contain other suitably packaged reagents and materials needed for amplification, for example, buffers, dNTPs, and/or polymerizing means, and for detection analysis, for example, enzymes and solid phase extractants, as well as instructions for conducting the assay.

In the course of their research, the inventors discovered, in one aspect, a novel and unobvious electrochemical real-time PCR (ERT-PCR) technique employing a solid support, e.g. silicon glass microchip, method for simultaneous DNA amplification and detection. This on-chip ERT-PCR process relies on the extension of oligonucleotides in either solution- and/or solid-phase(s) and the measurement of electrochemical, e.g. continuous or intermittent, signals in the presence of PCR reagents and enzymes. In one preferred implementation of the method of this invention, other parameters were adapted, including the passivation of electrode surfaces, and the mode of electrochemical scanning during the PCR process. During the course of their research, the inventors also found that the ERT-PCR's onset of the thermal cycle (about 3-5 cycles) where the analytical signal begins to be distinguishable from the background is much shorter than that of the fluorescence-based methods when employed for high template DNA detection ($3 \times 10^6$ copies/µL). By discovering the power of carefully controlling the concentrations of immobilized probe(s) and the polymerase enzyme, the inventors have made a critical improvement by reducing the initial template concentration of the on-chip ERT-PCR. One of the implementations of the ERT-PCR based method provided in this patent, preferably employs a microchip platform, optionally an electrode/microchip acting as a solid phase for the attachment of DNAs, that will become the standard in the industry for rapid DNA detection for POCT applications.

In view of the above, the present invention, in one aspect, relates to a novel and unobvious electrochemical or electron-based method for detecting and quantifying a target molecule(s) comprising a nucleic acid(s) and/or nucleic acid coupled molecule(s) comprising a polymerase chain reaction (PCR) procedure conducted so that the target molecule(s) is(are) placed in contact with an electrochemical and/or electrically conductive reporter(s) that is(are) annealed to the target molecule(s) in the presence of a conductive electrode surface, whereby upon PCR cycling the amplification of the target molecule(s) is measured by electrochemical detection. In one preferred implementation the method comprises a real time method. This invention addresses the deficiencies inherent in the prior art of optically, e.g. fluorescence, based real-time PCR method. It does this by utilizing a novel and unobvious strategy based on the combination of a redox-labeled reporter(s), amplicon(s) or probe(s), such as a nucleic acid(s) or nucleic acid coupled molecule(s), e.g. a probe comprising a peptide coupled to a peptide nucleic acid, and conducting the PCR reaction in the presence of an electrode capable of detecting the electrochemical signal emitted by the probe(s). In another preferred embodiment, the method and apparatus are suited for conducting the PCR reaction with the red-ox probe(s) on a solid phase, e.g. an electrode. This permits the electrochemical detection of the capture of the probe with redox markers by the PCR extended oligonucleotide(s) bound to the solid phase. In yet another preferred embodiment, the reaction is detected in real time.

The novel and unobvious technology as described above would be suitable principally for use in two types of electrochemistry-based real time PCR devices or instruments. The first is suitably a bench-top type, which will provide superior performance to currently available real-time instruments QPCR produced by, e.g. Applied Biosystem (ABI), Stratagene and Roche. Hospitals, research/testing/teaching laboratories, government lab for food/drug testing, among others require real time PCR instruments. The second type of instrument is a portable real-time PCR analyzer, a smaller, possibly handheld, device that permits the decentralized analysis of nucleic acid samples, such as those containing pathogens and the like. The followings are other applications for the method and device of this invention, including clinical diagnostics and scientific research uses. The portable real-time PCR analyzer provides a nucleic acid biosensor for decentralized and point-of-care testing including for genetic diseases analysis, viral quantification, pathogen identification, environmental monitoring, and drug monitoring, among many others.

Thus, this invention may also preferably be practiced by employing a microchip platform strategy. That is, the electrochemical detection of the red-ox marker probe binding to the amplified nucleic acid(s) may be carried out on a portable chip based system, and even more preferably in real time. This electrochemical apparatus and method employ simple and small size, e.g. miniature instrumentation that favorably compares to the bulky and sophisticated optics required in the fluorescence-based schemes. This invention may be used for the real-time detection of bioanalyte(s), e.g. water pathogens, such as $E.\ Coli$, in a decentralized environment.

In another aspect of the invention, the inventors have demonstrated for the first time that the extension of an electrode-bound oligonucleotide probe, for example with a labeled marker, e.g. deoxythymine triphosphate (dTTP) substituted by ferrocene-labeled deoxyuridine triphosphate (Fc-dUTP), may be utilized to monitor DNA amplification in real-time. Briefly, an oligonucleotide probe specific to a PCR target nucleic acid or amplicon was immobilized onto an electrode, e.g. an Indium Tin Oxide (ITO) electrode. The electrode was then dipped into a PCR solution in a conventional PCR tube format and denaturation was started to separate the strands of the target nucleic acid. During the subsequent annealing step, the heat-denatured, single-stranded target nucleic acid or amplicon hybridized to the probe bound to the ITO electrode. The probe was then extended by addition of polymerase enzyme in a solid-phase PCR producing a progressive accumulation of the redox marker, now captured in the extended DNA molecule coupled to the amplicon or target nucleic acid, onto the electrode surface. During the course of various experiments, multiple samples were run in parallel under identical conditions. The electrochemical or electric signal of the marker incorporated into the electrode bound amplified DNA, e.g. ferrocene signal, was then electrochemically measured.

In addition, the inventors investigated the effect on the electrochemical detection method of the invention of passivating the electrode surface, and the electrochemical scanning during the PCR amplification that greatly affect its performance. The ability to conduct real-time PCR in a microchip is critical to its practical application to a portable device for POCT applications. The inventors' approach minimizes background noise while at the same time enhances the electrochemical signal, particularly in a microchip format.

An underlying principle of one aspect of this invention is an electrochemistry-based real-time PCR method involving the use of 1) a solid-phase and/or a solution-phase extension of captured nucleic acid probes on a conductive electrode surface; 2) the incorporation of more and more electrochemical or electrically conductive reporters to the amplified nucleic acid bases as the number of PCR cycles increases, and 3) the integration of electrochemical detection and nucleic acid amplification on a micro-chip platform.

Solid-Phase Method

Figure 1:
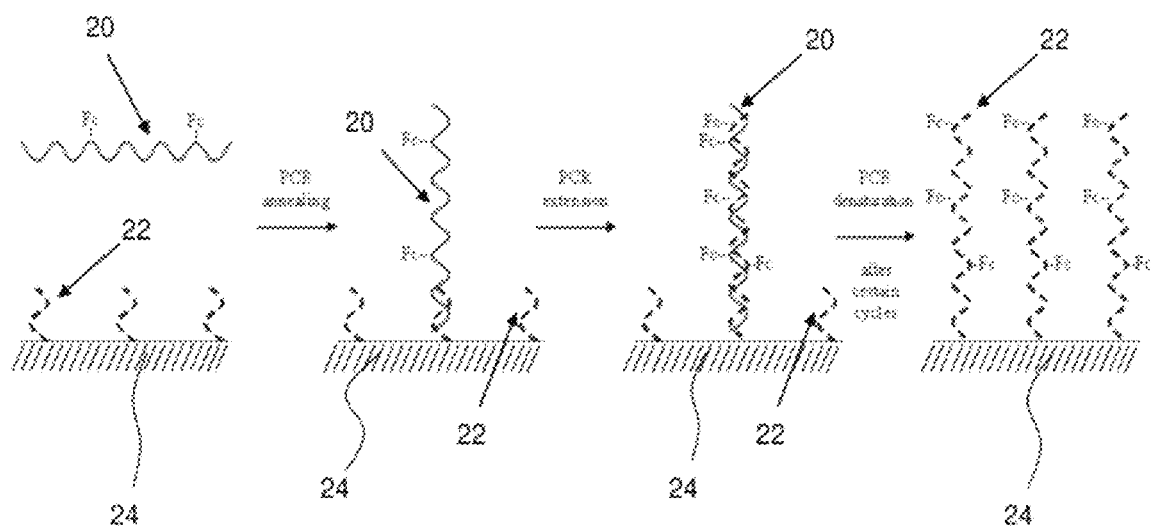
FIG. 1 shows a scheme of a solid-phase method employing a red-ox probe according to one embodiment of the present invention.
Figure 2A:
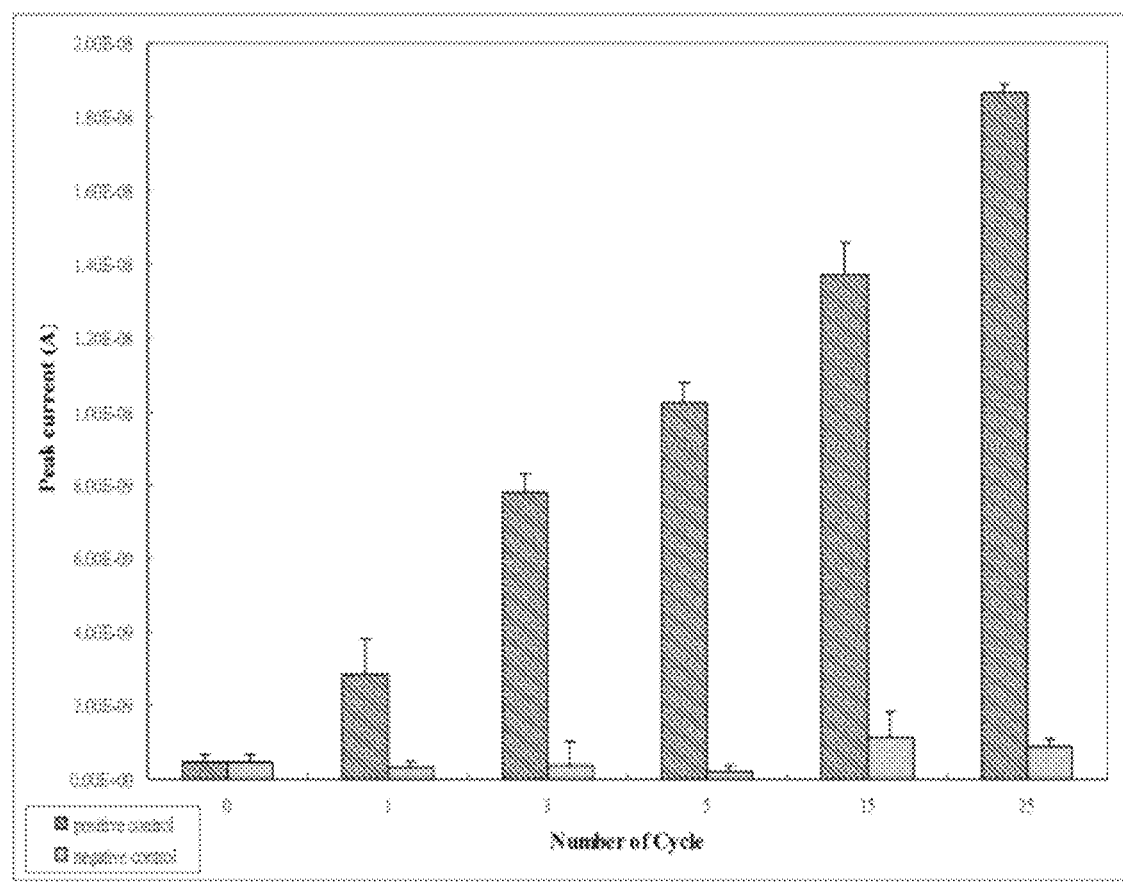
FIG. 2A provides a graph showing differential pulse signals of ferrocene at different PCR cycle numbers according to the same embodiment of the present invention.
Figure 2B:
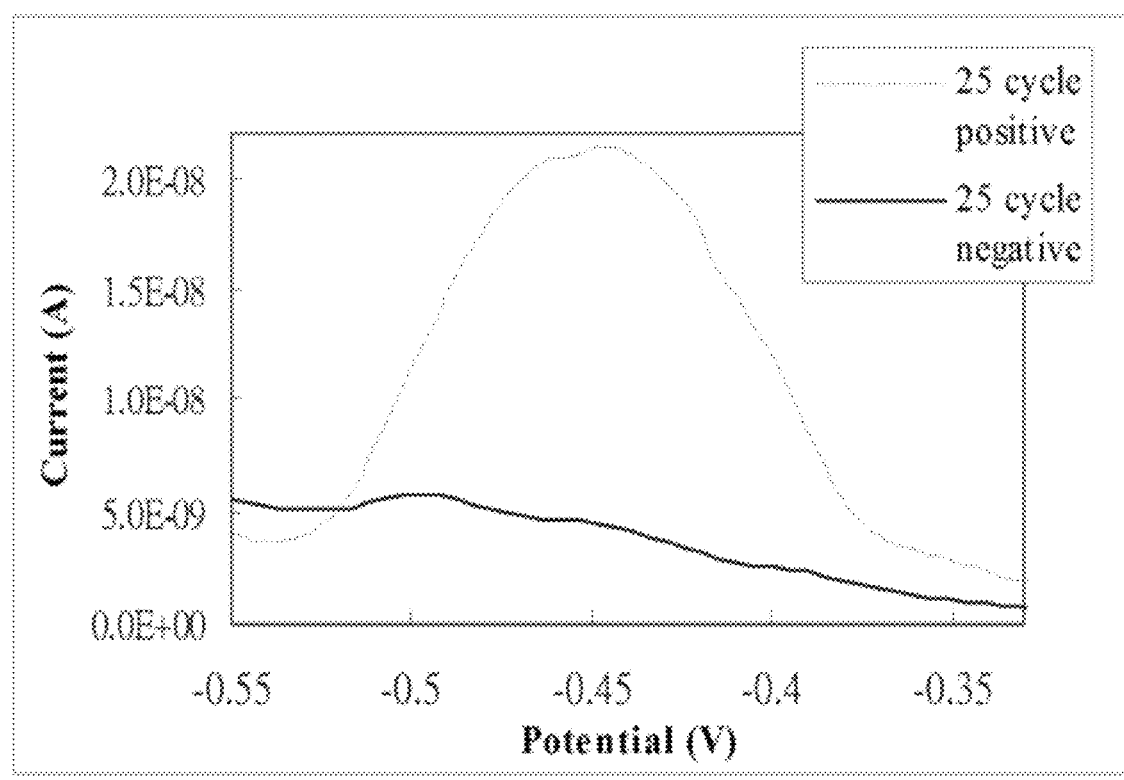
FIG. 2B shows a differential pulse voltammetric scan of the indium tin oxide (ITO) electrodes after 25-cycle PCR with (positive, broken line) or without (negative, solid line) the target template.

In one aspect, the instant invention provides the electrical or electrochemical (EC) real-time DNA detection method based on the solid-phase extension of the capture probe (in broken lines of FIG. 1) 22 with a labeled marker(s) such as, for example Fc-dUTP, Fc-dATP, Fc-dGTP or Fc-dCTP, among other electrically conductive molecules, as is schematically shown in FIG. 1. During the PCR denaturation step (preferably at about 95° C.), the double-stranded amplicon is denatured into a single-stranded form 20 (in solid lines of FIG. 1). At the annealing temperature (55° C.), the amplicon 20 hybridizes with the immobilized extension probe 22 in addition to the solution hybridization between the amplicon 20 and primers. Thereafter, the probe 22 is extended with the incorporation of Fc-dUTP by the polymerase. With this strategy, the redox signal, in proportion to the amount of amplicon, gradually builds up. The most prominent feature is the possibility to directly detect the electrochemical signal of the amplicon cycle-by-cycle. FIG. 2A shows the differential pulse voltammetric scan of the ITO electrodes after running different PCR cycles. The electrochemical signal from the incorporated Fc increases with the PCR cycle number. Control experiments, which either do not have the template or have nonspecific template, are studied to confirm that the detected electrochemical signal indeed originated from the specific extension of the immobilized probe, and the results are shown in FIG. 2B. A close-to-flat line signal was obtained for the negative control after 25 cycles. It should be noted that, at a starting template amount similar to the prior art optical based real time PCR, the onset spot (i.e., the point at which the signal is distinguishable from the baseline) for this EC scheme occurs earlier than that for the optical one (usually at 15 to 20 cycles). This is particularly attractive for ultra-fast DNA identification in point-of-care applications.

More particularly, the present invention provides a real time solid phase method for electrochemically or electrically monitoring or quantifying the amount of nucleic acid(s) in a biological sample by formation of a polymerase chain reaction (PCR) produced polynucleic acid(s), that comprises the steps of:

contacting a sample comprising a target nucleic acid(s) ends, a solid surface bound probe(s) comprising a first primer(s) provided with a sequence(s) that is complementary to at least a portion of one end of the target nucleic acid(s), a second primer(s) in solution that is(are) complementary to at least a portion of the opposing end of the target nucleic acid(s), and an electrochemically or electrically conductive marker(s) that is(are) adapted for incorporation into a polynucleic acid(s) by chain polymerization and when incorporated thereof produces a signal(s) change(s) if subjected to an electric potential;

adding a polymerase chain reaction enzyme(s) under conditions effective for PCR amplification to occur;

applying an electric potential to the sample and detecting or measuring in real time the electric signal(s) produced by the labeled marker(s) incorporated into the solid surface bound probe(s); and quantifying the amount of nucleic acid(s) present in the sample and the amount of polynucleic acid(s) produced by correlating the change(s) in signal(s) over time with the formation of polynucleic acid(s).

In a preferred implementation, the first primer(s) is(are) immobilized onto the solid surface. In a more preferred implementation, the method provided by the present inventors may also include a step of denaturing the target nucleic acid(s) prior to polymerization, and preferably the PCR step is conducted with a PCR enzyme that is thermo-stable.

In another preferred implementation, the signal(s) change may comprise a change of current intensity, which in all likelihood will be proportional to the concentration of the polynucleic acid(s) produced and of nucleic acid(s) in the sample.

This method may be employed by running more than one PCR amplification cycle. Clearly, in this mode of the method each signal change is associated with or proportional to the amount of polynucleic acid(s) formed in each PCR amplification cycle. In yet another preferred implementation, the electric signal may be detected and/or its value measured with at least a pair of conductive electrodes placed in the sample. Multiple pairs of electrodes may also be employed as described herein.

In one preferred implementation, the surface of at least one of the conductive electrode(s) comprises indium tin oxide, gold, platinum, or carbon.

In an even more preferred implementation, probes may be bound onto the conductive electrode surface. In this type of method, the labels may comprise ferrocene and ferrocene derivatives, as well as others that an artisan would recognize.

In another preferred implementation, examples of markers are dUTP, dATP, dGTP, or dCTP, as well as others that are capable of accepting an electrochemical label and are suitable for incorporation in DNA amplification by PCR.

Also provided by this patent is a microchip that in its simple form comprises an electrochemically or electrically conductive electrode; and a solid support adapted to receive a molecule comprising a nucleic acid(s) wherein the microchip is adapted to be used for the solid-phase extension method as described above. The nucleic acids may be added to the solid support at the laboratory end, or the substrates may be purchased already having coupled thereto a specific probe, as desired. Laboratory techniques for attaching DNA to a solid support as well as suitable materials for the support are known in the art and need not be described in details herein. An example of solid support material is glass. In another embodiment, the microchip has an electrode that is provided with a surface comprising the solid support; that is the electrode itself is adapted for receiving the DNA. The microchip may also have integrated therein for monitoring the PCR amplification a temperature sensor(s) comprising or being formed of a metal, and a micro heater(s). The temperature sensor(s) is typically formed of or comprises platinum. However, other metals such as gold and copper, and materials exhibiting the function of temperature monitoring are also suitable. In terms of the electrodes provided with the device and/or for the microchip, the surface of at least one of them is typically formed of or comprises indium tin oxide, but other metals such as gold and platinum, or other electrically conductive materials can also be used. The electrode or a surface thereof may be patterned and integrated into the microchip.

Yet another embodiment of the invention further provides a microchip, that comprises a glass substrate wherein an electrochemically or electrically conductive electrode(s) is(are) patterned; and a silicon chip wherein a temperature sensor(s) and a micro heater(s) are integrated. In this embodiment, the silicon chip is adapted to be bonded with the glass substrate in a way to create a microchamber therebetween such that the polymerase chain reaction (PCR) is carried out and monitored within the microchamber.

In a further embodiment, the microchip of this patent may be incorporated into a device for measuring electrochemical or electric signals. This device may be of bench top proportions similar to other devices and analyzers employed in the art, or in a novel and preferred embodiment it may be a portable device, preferably of substantially having reduced size when compared to bench-top devices. Clearly, an advantage of the present technology is the ability to produce accurate and effective analyzers and devices of a reduced size suitable for use at point-of-care sites.

In order to practice the method and employ the device/analyzer of this invention, the inventors are also providing an electrochemical signal detection kit that comprises a plurality of PCR primers, and one or a plurality of microchip(s) of the invention. The kit may further include PCR reagents other than primers. These kits are optionally included with the sale of the device or analyzer, either the bench-top or the portable variety.

Solution-Based Method

In a further aspect, the inventors develop a novel competition-based electrochemical DNA detection method, utilizing solution-phase competitive hybridization instead of interfacial competitive hybridization. This is achieved by introducing a second DNA probe into the immobilization-free DNA detection scheme previously developed by the inventors and described in Luo, X., et al. (Anal. Chem. 2008). As illustrated in FIG. 8, in the solution-phase competition-based electrochemical DNA detection scheme, a DNA probe (p-DNA) 102 fully complementary to the target DNA (t-DNA) 106 is used, as well as a ferrocene-labeled PNA (Fc-PNA) 104 in which the PNA therein 104a has a sequence identical to part of the t-DNA 106 (in other words, complementary to a segment of the p-DNA 102). When no t-DNA 106 is present, the Fc-PNA 104 will hybridize with the p-DNA 102. No Fc signal would be observed as the electrostatic repulsion between the negative electrode surface 108 and the negative Fc-PNA/p-DNA hybrid 110 prevents the Fc 104b from approaching the electrode 108. In the presence of t-DNA 106, the t-DNA 106 with a longer sequence than that of the Fc-PNA 104 possesses a higher binding affinity to p-DNA 102 and therefore the competition between t-DNA 106 and Fc-PNA 104 for hybridization with p-DNA 102 would result in the production of free Fc-PNA 104, leading to the increase of Fc 104b redox signal (signal-on).

Unlike the hybridization in immobilization-based DNA detections which occur on a solution-electrode interface, the hybridization in this novel immobilization-free scheme occurs in a homogeneous solution phase and greatly reduces the assay time. More reliable results can be produced by this signal-on immobilization-free electrochemical DNA detection than those from the aforesaid previously developed signal-off method.

In particular, the instant invention provides a solution phase method for electrochemically or electrically detecting target nucleic acid(s), comprising the steps of:

a). providing a sample comprising a first probe(s) having the same electrical polarity as that of an electrode surface such that the first probe(s) is(are) repelled from the electrode surface; and a second probe(s) comprising an electrochemically or electrically conductive labeled marker(s) coupled to an electrically neutral molecule(s), the second probe being operatively linked to the first probe(s);

b). providing the target nucleic acid(s) to the sample wherein the first probe(s) is(are) complementary to at least a portion of the target nucleic acid(s); and c). applying an electric potential to the sample and detecting or measuring a signal(s) produced by the labeled marker(s);

wherein when the first probe(s) is(are) hybridized with the target nucleic acid(s), the second probe(s) is (are) released from the first probe(s) and the labeled marker(s) is(are) freely diffused to the electrode surface to produce a signal intensity change(s) when subjected to an electric potential, and such signal intensity change(s) correspond(s) to the target nucleic acid(s) in the sample.

In one preferred implementation, the method further comprises the step of:

d). quantifying the amount of the target nucleic acid(s) present in the sample by correlating the signal intensity change(s) over time with the amount of the target nucleic acid(s) present.

In another preferred implementation, step (a) further comprises the step of applying an electric potential to the sample.

In a preferred implementation, the hybridization time is around 5 minutes.

In a preferred implementation, the melting temperature of the hybridized target nucleic acid(s) and first probe(s) is higher than that of the hybridized second probe(s) and first probe(s). In another preferred implementation, the target nucleic acid(s) comprises a longer sequence than that of the second probe(s).

In yet one preferred embodiment, the first probe(s) is(are) fully complementary to the target nucleic acid(s); in another preferred embodiment, the second probe(s) is(are) complementary to at least a portion of the first probe(s).

In one preferred implementation, the labeled marker(s) comprise(s) ferrocene, ferrocene derivatives, or any combination thereof. In yet another preferred implementation, the electrically neutral molecule(s) comprise(s) a peptide nucleic acid(s).

In one preferred implementation, signal(s) produced by the labeled marker(s) is(are) electric signal(s).

In another preferred implementation, electrode surface is made of a material comprises indium tin oxide, gold, platinum or carbon. In yet another preferred implementation, the electrode(s) comprise(s) interdigitated array electrode(s).

In one preferred implementation, the target nucleic acid(s) comprise(s) an electrically negatively charged DNA(s); the first probe(s) comprise(s) an electrically negatively charged DNA(s) and is(are) fully complementary to the target nucleic acid(s); the second probe(s) comprise(s) a ferrocene-labeled peptide nucleic acid(s); and the electrode surface is electrically negatively charged.

In yet a preferred implementation, the target nucleic acid(s) is(are) produced in a polymerase chain reaction (PCR) further comprises the step of quantifying the amount of said target nucleic acid(s) produced by correlating the change(s) in signal(s) over time with the formation of said target nucleic acid(s).

Also provided by this patent is a microchip that in its simple form comprises an electrochemically or electrically conductive electrode provided on a surface adapted to receive a molecule comprising a target nucleic acid(s) wherein the microchip is adapted to be used for the solution-phase method as described above. In one embodiment, the surface comprises a solid; an example of solid support material is glass. In another embodiment, the electrode itself is adapted for receiving the DNA. The microchip may also have integrated therein for monitoring the PCR amplification a temperature sensor(s) comprising or being formed of a metal, and a micro heater(s). The temperature sensor(s) is typically formed of or comprises platinum. However, other metals such as gold and copper, and materials exhibiting the function of temperature monitoring are also suitable. In terms of the electrodes provided with the device and/or for the microchip, the surface of at least one of them is typically formed of or comprises indium tin oxide, but other metals such as gold and platinum, or other electrically conductive materials can also be used. The electrode or a surface thereof may be patterned and integrated into the microchip.

Yet another embodiment of the invention further provides a microchip, that comprises a glass substrate wherein an electrochemically or electrically conductive electrode(s) is(are) patterned; and a silicon chip wherein a temperature sensor(s) and a micro heater(s) are integrated. In this embodiment, the silicon chip is adapted to be bonded with the glass substrate in a way to create a microchamber therebetween such that the polymerase chain reaction (PCR) is carried out and monitored within the microchamber.

In one embodiment, the target nucleic acid(s) comprise(s) an electrically negatively charged DNA(s); the first probe(s) comprises an electrically negatively charged DNA(s) and fully complementary to the target nucleic acid(s); the labeled marker(s) comprises a ferrocene-labeled peptide nucleic acid(s); and the electrode surface is electrically negatively charged.

In a further embodiment, the microchip of this patent may be incorporated into a device for measuring electrochemical or electric signals. This device may be of bench top proportions similar to other devices and analyzers employed in the art, or in a novel and preferred embodiment it may be a portable device, preferably of substantially having reduced size when compared to bench-top devices. Clearly, an advantage of the present technology is the ability to produce accurate and effective analyzers and devices of a reduced size suitable for use at point-of-care sites.

In order to practice the method and employ the device/analyzer of this invention, the inventors are also providing an electrochemical signal detection kit that comprises a plurality of PCR primers, and one or a plurality of microchip(s) of the invention. The kit may further include PCR reagents other than primers. These kits are optionally included with the sale of the device or analyzer, either the bench-top or the portable variety.

Kits similar to the ones described for the earlier method are also contemplated in this patent, and may contain all necessary components for the practice of the invention, such as primers, microchip, electrodes, PCR reagents, and the like. When provided immediately prior to its utilization the kits may also contain a labeled marker(s), and other custom made reagents.

The inventors successfully demonstrated the implementation of the ERT-PCR process in an integrated silicon-glass microchip. Key aspects of optional aspects of the invention, such as electrode surface passivation, effect of potential scanning on the fidelity of the electrochemical detection platform, quantification performance, as well as effects of enzyme and probe concentrations on the signal-to-background ratio are discussed in details. This new and unobvious nucleic acid detection method is far superior to the state-of-the-art fluorescence-based real-time PCR techniques in terms of speed and portability. With the design of multiple working electrodes on a single microchip in one of the embodiments of this invention, this technique is also very promising for real-time multiplexing detection. This invention provides a leap forward in method and device design for the incorporation of functional sample preparation onto a miniaturized device. The present method and device offer a superior technology for application to point-of-care nucleic acid analysis.

The examples presented below are intended to be illustrative of the various methods and compounds of the invention, but not to be limiting the present invention.

EXAMPLES

Example 1

Solid Phase Method

All general chemicals were obtained from Sigma-Aldrich (St. Louis, Mo.). All PCR reagents were purchased from Invitrogen (Carlsbad, Calif.), unless otherwise stated.

Example 1.1

Preparation of Solid Substrate

Indium tin oxide (ITO)-coated glass (Delta Technologies, Stillwater, Minn.) was first immersed in a solution of $H_2O_2$/$NH_4OH$/$H_2O$ (1:1:5) at 80° C. for 5 minutes. Then, it was rinsed with water and dried with nitrogen gas. The hydrolyzed substrate was treated with a 10% (3-glycidoxypropyl) trimethoxysilane in 95% ethanol for 1 hour. After silanization, the substrate was dried at 50° C. under vacuum.

Example 1.2

Attachment of Probe to Solid Substrate

A substrate prepared as shown in Example 1 above was incubated with 1 µM of an oligonucleotide probe of sequence: 5'-$NH_2$-TTT TTT TTT TTT TTT TTT TTA AGG AAA CAG CTA TGA C-3' (SEQ. ID NO. 1) in phosphate buffer saline (PBS, 100 mM NaCl/10 mM sodium phosphate, pH 7.0) overnight. Excess probes were washed off with PBS. The residual epoxide groups were blocked with ethanolamine for 30 minutes and washed again by PBS.

Example 1.3

PCR Amplification of Target Nucleic Acid

The PCR master mix contained 1× ThermoPol reaction buffer (20 mM Tris-HCl, 10 mM $(NH_4)_2SO_4$, 10 mM KCl, 2 mM $MgSO_4$, 0.1% Triton X-100, pH 8.8), 0.2 mM dNTPs (with 0.06 mM dTTP substituted by Fc-dUTP), 0.2 µM forward primer 5'-GTA AAA CGA CGG CCA G-3' (SEQ ID NO. 2), 0.2 µM reverse primer 5'-AAG GAA ACA GCT ATG AC-3' (SEQ ID NO. 3), 0.02 ng/µL M13mp18 template (Sigma), 0.5 µg/µL bovine serum albumin, and 0.02 units/µL Vent$_R$® (exo-) DNA polymerase (New England BioLabs, Ipswich, Mass.).

The functionalized ITO chip was dipped into the mixture and subjected to the following thermal cycling profile:
 initial denaturation at 95° C. for 2 minutes;
 25 cycles at 95° C. for 20 seconds, at 55° C. for 20 seconds, and at 72° C. for 10 seconds.

Example 1.4

Synthesis of Ferrocene-dUTP Labeled Marker

Fc-dUTP was synthesized according to the King et al. protocol (Wlassoff, W. A.; King, G. C., Nucleic Acids Res. 2002, 30, e58), with minor modification on the purification procedure to improve the yield. After certain PCR cycles, the ITO-coated chip was removed from the PCR tube and rinsed with water.

Differential pulse voltammetric measurements were performed using Autolab PGSTAT30 (Eco Chemie, The Netherlands) with a pulse amplitude of 100 mV and scan rate of 25 mV/s. Pt was used as the counter and pseudo-reference electrodes.

The thermal control system for the PCR consisted of a data acquisition card (PCI-MIO-16E-1, National Instruments, Austin, Tex.) along with a signal conditioning board (SC-2042-RTD, National Instruments) connected to the temperature sensors.

A digital feedback proportional-integral-derivative (PID) control algorithm was implemented in LabVIEW software (National Instruments) to control voltage supply to the heater by a power source (HP6629A, Hewlett-Packard, Rockville, Md.).

Electrochemical measurements were performed with an Autolab PGSTAT30 potentiostat/galvanostat (Eco Chemie, The Netherlands) controlled by the General Purpose Electrochemical System (GPES) software (Eco Chemie).

Example 1.5

Fabrication of Silicon-Glass Microchip

Figure 3A:
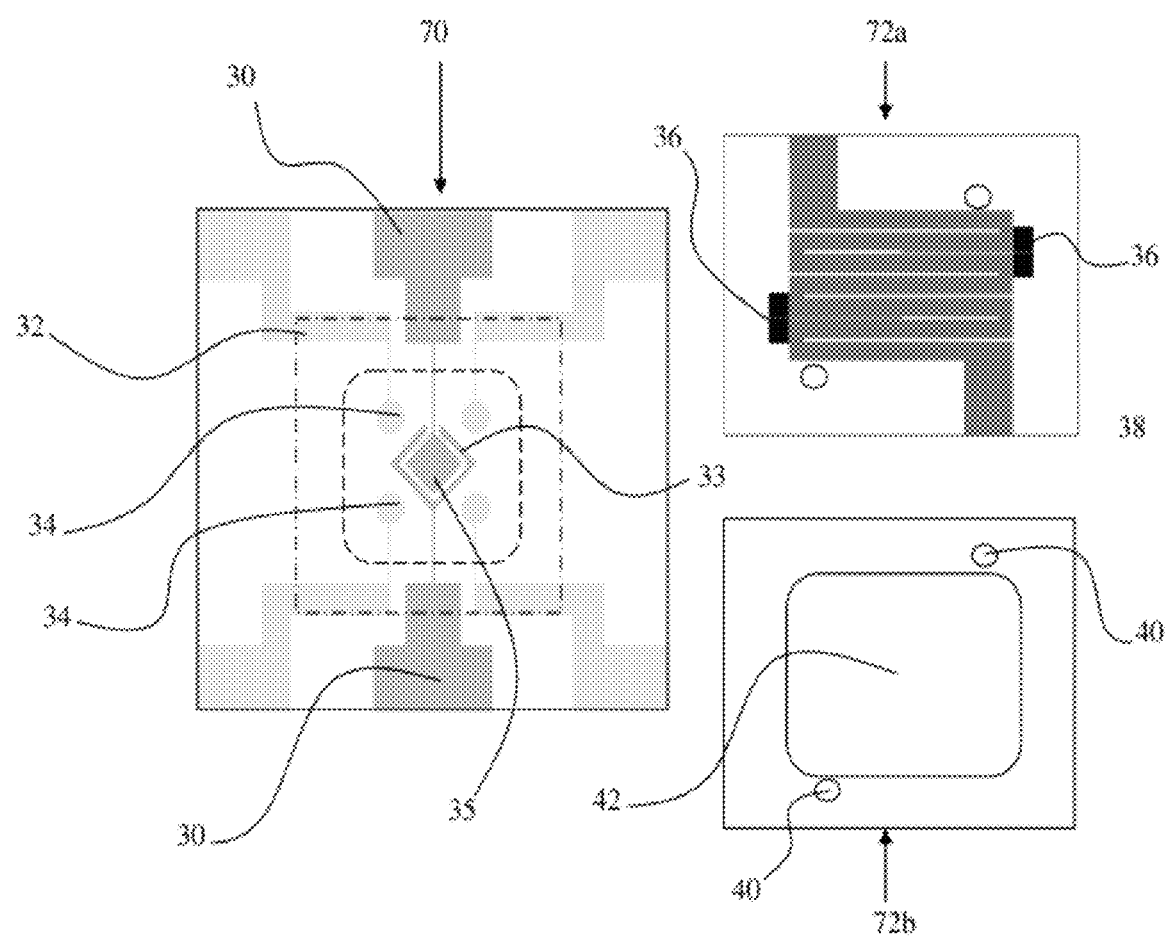
FIG. 3 is a schematic diagram showing (A) the layout of the silicon and glass substrates; (B) initial state of the oligonucleotide capture probe modified ITO electrode prior to the PCR.
Figure 3B:
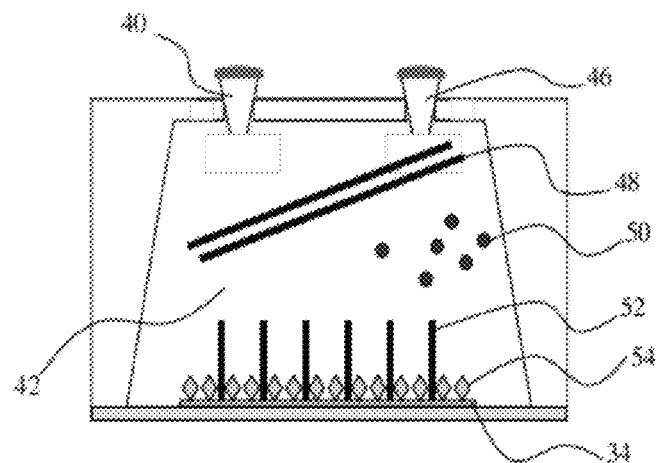
Figure 3C:
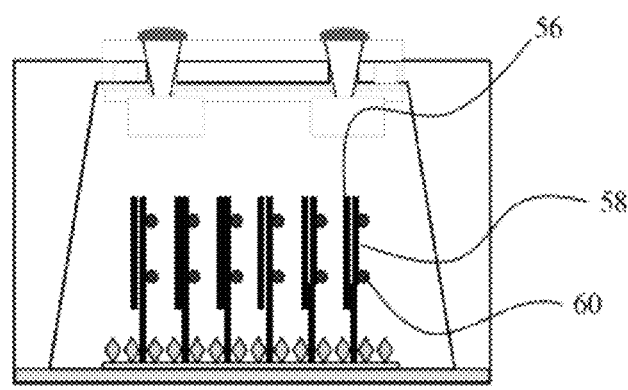

An integrated silicon-glass microchip consisted of silicon (Si) (thickness of 400 µm) and ITO-coated glass substrates (Delta Technologies, Stillwater, Minn.) with metallic patterns and microstructures. See, FIGS. 3A, 3B, and 3C provided with this patent.

Thin film platinum (Pt) heaters 38 and temperature sensors 36 (thickness of 100 nm) were patterned on the front side of the Si chip 72a, for PCR thermal cycling and the microreactor 42 (length and width of 5 mm, depth of 325 µm) for DNA amplification, etched by the inductively coupled plasma-deep reactive ion etching (ICP-DRIE) process, was located on the back of the Si chip 72b. ICP-DRIE etched feed holes 40 (diameter of 500 µm, depth of 100 µm) on the back side of the Si chip 72b were used for the injection and removal of PCR solution.

The ITO-coated glass chip 70 had thin film Pt pseudo-reference and counter electrodes 30 (thickness of 100 nm) on the center surrounded by four ITO-based (thickness of 100 nm) circular working electrodes 34 for probe immobilization and solid-phase extension of the oligonucleotide capture probe.

Ultra-violet (UV) curing optical cement (Type UV-69, Summers Optical, Hatfield, Pa.) was used to seal the silicon 72 and glass chips 70 (with the silicon chip 72 being placed on the glass chip 70 at the location 32) and the curing procedure was done according to the manufacturer's instruction, and obtained as similarly reported by the inventors previously for the multiplexed detection of *Escherichia coli* and *Bacillus subtilis*. See, Yeung, S. W.; Lee, T. M. H.; Cai, H.; Hsing, I. M. Nucleic Acids Res. 2006, 34, e118.

Example 1.6

Probe Immobilization and Electrode Passivation

Prior to the UV bonding, the patterned glass substrates were sequentially sonicated in an Alconox solution (8 g of Alconox per liter of water), propan-2-ol, and twice in water, with each sonication lasting for 15 minutes. Then, they were dried with nitrogen gas and treated in a plasma cleaner (Harrick Plasma, Ithaca, N.Y.) for 10 minutes.

The hydrolyzed glass substrates then were immersed in a 10% (3-glycidoxypropyl)trimethoxysilane (dissolved with 95% ethanol) for 1 hour. The silanized substrates were dried at 50° C. under vacuum for 3 hours and bonded with the silicon substrate. After the UV bonding, a 1 μM oligonucleotide probe solution of sequence: 5'-$NH_2$-TTT TTT TTT TTT TTT TTT TTA AGG AAA CAG CTA TGA C-3' (SEQ. ID NO. 1) in phosphate buffered saline (PBS, 100 mM NaCl/10 mM sodium phosphate, pH 7.0) was introduced into the microchamber and incubated overnight. Excess probes were washed off with PBS. Residual epoxide groups were blocked with ethanolamine for 12 hours, unless otherwise stated.

Finally, the microchamber was flushed thoroughly with autoclaved double-deionized water and dried with nitrogen gas.

Example 1.7

Example of Electrochemical Real-Time PCR Method

The PCR master mix contained 1× ThermoPol reaction buffer (20 mM Tris-HCl, 10 mM $(NH_4)_2SO_4$, 10 mM KCl, 2 mM $MgSO_4$, 0.1% Triton X-100, pH 8.8), 0.2 mM dNTPs (with 0.06 mM dTTP substituted by Fc-dUTP), 0.2 μM forward primer 5'-GTA AAA CGA CGG CCA G-3' (SEQ ID NO. 2), 0.2 μM reverse primer 5'-AAG GAA ACA GCT ATG AC-3' (SEQ ID NO. 3), 0.04 ng/μL M13mp18 template, 0.5 μg/μL bovine serum albumin, and 0.04 units/μL Vent$_R$® (exo-) DNA polymerase (New England Bio Labs, Ipswich, Mass.).

Referring to FIGS. 4B and 4C, the master mix was pipetted into the microchamber 42 and the injection holes 40 were sealed with Bostik's Blu-Tack. The chip was subjected to the following thermal cycling profile: initial denaturation at 94° C. for 2 minutes; 30 cycles at 94° C. for 20 seconds; at 55° C. for 20 seconds; 72° C. for 10 seconds. Apart from on-chip thermal control by the patterned heater 38 (shown in FIG. 3A) and temperature sensors 36 (shown in FIG. 3A), the PCR thermal cycling of the microchip could also be done by the conventional cycler (Eppendorf® Mastercycler® personal) with very similar results (data not shown). Differential pulse voltammetric measurements were performed with pulse amplitude of 100 mV and scan rate of 25 mV/s.

Example 1.8

Results

A schematic of the electrochemical real-time PCR (ERT-PCR) method conducted on a silicon-glass microchip is shown in FIGS. 3B and 3C of this patent. It is important for the successful implementation of on-chip ERT-PCR to make successful readings of accumulative electrochemical signal produced by the increased amount of PCR amplicon at each PCR thermal cycle.

This method is unlike the ERT-PCR conducted in an Eppendorf® tube PCR process. See, Yeung, S. W.; Lee, T. M. H.; Hsing, I. M. J. Am. Chem. Soc. 2006, 128, 13374-13375. This on-chip ERT-PCR process involves oligonucleotide extension of solution- and solid-phases in a closed microenvironment, and repetitive electrochemical potential scanning without removal of solution and surface-adsorbed impurities. Several crucial factors, e.g. passivation of the sensing electrode, strategy on the electrochemical scanning, and control of enzyme and oligo probe concentrations, that would greatly affect the analytical signal of this new assay platform are discussed in the following paragraphs.

Electrode Surface Passivation

One of the biggest challenges in running ERT-PCR in a microchip format is to minimize, if not totally eliminate, the background signal caused by the solution-phase Fc-dUTP. FIG. 4 shows that the background signal is strongly dependent on the duration of the ethanolamine blocking step. Characteristic redox peaks from Fc-dUTP 50 (shown in FIG. 3B) (~+0.57 V vs. Pt pseudo reference electrode) are noticeable with blocking time shorter than 3 hours (curve c on FIG. 4), which is likely caused by the nonspecific adsorption of the Fc-dUTP 50 to the unreacted epoxide groups and/or free diffusion of the Fc-dUTP 50 to the ITO surface 34 (shown in FIG. 3B). For a long enough blocking time, i.e., 12 hours (curve d on FIG. 4), the baseline is nearly flat. This implies that almost all the residual epoxide groups are reacted with the ethanolamine so that nonspecific adsorption and diffusional access of the Fc-dUTP 50 to the electrode surface 34 is minimized. With this, the signal-to-noise ratio is significantly increased and hence a lower detection limit is expected. When practicing this method, no washing step is required to remove the free soluble markers from the solution and the method, therefore, achieves real-time PCR quantification.

Electrode Scanning

The method described herein is different from the fluorescence-based real-time PCR, ERT-PCR methods. The present method requires electrochemical scanning during or at intermittent interval during the thermal cycling process in order to "electrochemically" monitor the amplification into PCR products in a "real-time" setting. In one of the embodiments, there are four circular ITO-based electrodes 34 patterned in our silicon-glass microchip 70. See, FIG. 3A showing this patent.

It is desirable to have each electrode scanned for a plurality of times, e.g. once for every PCR cycle and 30 times in a 30 cycle PCR, without affecting the PCR performance. However, in fact the adsorption characteristics of a charged species, e.g. dNTPs, $Mg^{2+}$, and of the polymerase enzyme may change when exposed to repetitive potential scanning, a subtle change that might affect the nucleotide extension on the solid electrode surface.

To investigate the effect of electrochemical scanning, the ERT-PCR process was performed on microchips with all the ITO electrodes being immobilized with the same capture oligonucleotide probes. In one set of the microchips, all four ITO electrodes were electrochemically scanned for multiple times per every five cycles; while in the other chips, the four ITO electrodes were selectively and singly scanned at the thermal cycle of 0th, 10th, 20th and 30th, respectively.
Superiority Over Fluorescent-Based Method As may be seen from FIG. 5A, a cycle-by-cycle increase of the electrochemical signal was obtained, indicating a successful incorporation of the Fc-dUTP redox marker on the extended probe. A low background noise for the amplification case without DNA template (curve c of FIG. 5A) suggests effective minimization of the unspecific electrochemical interference. With an initial template concentration of $3 \times 10^6$ copies/µL, the "onset" cycle number at which the analytical signal in ERT-PCR (~3-5 cycles) is distinguishable from the background signal is much smaller than that for the fluorescence-based real-time PCR counterparts (usually 15-25 cycles). See FIGS. 6A and 6C for comparison. This suggests that fewer PCR cycles are needed for the ERT-PCR technique. It should be noted that fluorescence-based methods are known to detect a very low template concentration. The present strategy for reducing the required initial template concentration is discussed below.

The leveling-off gain of the electrochemical signal at high cycle numbers (data points in squares, curve b of FIG. 5A) on the multiply-scanned electrode is a clear indication that the multiple electrochemical scanning indeed may have an adverse effect to the process as compared to the signal measured on the single scanning electrode (data points in circle, curve a of FIG. 5A). Actually, similar plots of signal saturation at high cycle numbers were also observed when employing a fluorescence-based real-time PCR method of signal measurement.

However, the reasons associated with signal saturation in these two methods are very likely of a very different nature. In the fluorescence-based method, the phenomena may be attributed to the depletion of limiting reagents, while in the present ERT-PCR method, it is most likely associated with electrochemical scanning itself although the actual mechanism of the potential scanning is not yet fully understood. Nevertheless, the experimental results strongly suggest that the effect of multiple scanning may be reduced by adding more polymerase (data not shown). One possibility to explain these results is that irreversible adsorption of enzyme and other species on the electrode may play a role in the process.

Although multiple scanning may have an impact on the on-chip ERT-PCR process, it is possible to avoid it by having more ITO-based working electrodes in the microchip and/or using each of the electrodes for a single scanning purpose at a specific thermal cycle(s). The linear relationship of the signal and the cycle number in the single-scanning measurement (curve a, FIG. 5A) reflects this strategy. See, for example FIG. 5A of this patent. Therefore, the experimental data presented in the remaining Examples were obtained based on a single-scanning electrode. Actually, density of the immobilized probe on the electrode may also affect the electrochemical signal in ERT-PCR process, the implications of which are discussed in later paragraphs.
Calibration Plot For any real-time PCR technique, it is important to evaluate its performance in the quantification of target DNA molecules (target nucleic acids). In the ERT-PCR method of the invention, the standard curves as shown in the FIG. 6B were obtained by setting the threshold value at 0.1 nA for the current-cycle number plots with different initial template concentrations. Rather than the linear calibration plot required by fluorescence-based real-time PCR methods, the electrochemical calibration plot may be approximated by doing two linear regimes, with a crossover point at about $10^5$ copies/µL. See, for instance FIG. 6B of this patent. It should be noted that the electrochemical real-time PCR method provides a superior performance, e.g. in terms of the threshold cycle number, than the state-of-the-art fluorescence-based real-time PCR method at high template concentrations (>$10^5$ copies/µL).

Referring back to FIG. 6A, for template concentrations lower than $10^4$ copies/µL (curves a and b), the threshold cycle number of the present electrochemical method exceeds that of any fluorescence-based methods, possibly due to competition between the solution phase primer and the immobilized probe for the target amplicon. At low target copy number, the solution phase primer tends to dominate during the annealing step. Hence, it may be necessary to build up sufficient amount of PCR products (polynucleic acids) to facilitate solid phase probe extension, which may lead to a need for a large threshold cycle number in cases of low initial DNA (target nucleic acid) sample content.
Effects of Enzyme and Probe Concentrations on Peak Current Signals As already discussed, the PCR threshold cycle number required for low template concentration samples is likely higher. In the fluorescence-based methods, little may be done to increase the signal-to-background ratio given that background fluorescence is not easily eliminated. On the other hand, the enzyme and probe concentrations may be used to enhance the sensitivity of the ERT-PCR method of the invention. FIG. 5B provided with this patent shows that the analytical signals may be greatly increased by increasing enzyme concentrations (without increase in the background signals, data not shown). An increase of 8 times in the enzyme concentration produces an 8-fold increase in the analytical signal. More importantly, at initial template concentrations of $3 \times 10^3$ copies/µL, the threshold cycle number is reduced from 25 to less than 5.

Another way to improve the signal-to-background ratio may be achieved by using a higher probe concentration during the immobilization step. See, FIG. 7 of this patent. The probe concentration during the immobilization step for all previous experiments is 1 µM. When the concentration is raised to 100 µM, the analytical signal increases by a factor of 8.

Example 2

Solution Phase Method

Example 2.1

Materials

Ferrocene-labeled PNA (Fc-PNA) was purchased from PANAGENE (Korea), with the following structure: Fc-O-AACCACCACCA-NH$_2$ (11-mer; SEQ ID NO. 4), where Fc and O denote a ferrocene moiety and an ethylene glycol linker, respectively. The DNA probe (p-DNA) with a sequence of 5'-TGGTGGTGGTTCTGGTGGCG-3' (20-mer; SEQ ID NO. 5), target DNA (t-DNA) with a sequence complementary to p-DNA 5'-CGCCACCAGAAC-CACCACCA-3' (20-mer; SEQ ID NO. 6) and a non-complementary DNA (nc-DNA) with a sequence of 5'-CTCAAC-CTCCTGTCAATGC-3' (19-mer; SEQ ID NO. 7) were purchased from Integrated DNA Technologies (USA). Bovine Serum Albumin (BSA) and the hybridization buffer (20 mM Tris-HCl, 10 mM $(NH_4)_2SO_4$, 10 mM KCl, 2 mM $MgSO_4$, 0.1% Triton X-100, pH 8.8) were purchased from New England Biolabs (USA). All other chemicals used were of analytical reagent grade. All aqueous solutions were prepared with deionized water (specific resistance>18.2 MΩ/cm) and obtained with a Milli-Q reagent grade water system (Millipore, USA). Electrochemical measurements were performed with an Autolab PGSTAT30 potentiostat/galvanostat (Eco Chemie, The Netherlands) controlled by the General Purpose Electrochemical System (GPES) software (Eco Chemie).

Example 2.2

Fabrication and Preparation of Electrodes

The electrochemical measurements were conducted on an indium tin oxide (ITO) coated glass chip 70 as shown in FIG. 3A. The chip has four patterned circular ITO spots serving as working electrodes 34, a Pt counter electrode 35, and a Pt pseudo-reference electrode 33. Each of the four ITO working electrodes 34 has an active surface area of $7.85 \times 10^{-3}$ $cm^2$. In one preferred embodiment, for electrochemical measurements, 2 µL of sample is enough to cover one of the ITO working electrodes 34, the Pt counter electrode 35, and the Pt pseudo-reference electrode 33. The potential of the Pt pseudo-reference electrode 33 in the hybridization buffer was determined to be +0.36 V with respect to an Ag/AgCl reference electrode.

The chip 70 was fabricated by microfabrication. Briefly, photoresist was coated onto the ITO-coated glass (Delta Technologies, Stillwater, Minn.) and patterned by photolithography. After the selective etching of ITO, the desired working electrode pattern was formed. Then, a second photolithographic step was performed and Pt was sputtered onto the patterned photoresist. After a lift-off process, patterned Pt was obtained.

Before each electrochemical measurement, the chip 70 was cleaned to obtain a negatively-charged surface. Briefly, it was sequentially sonicated in an Alconox solution (8 g of Alconox/L of water), propan-2-ol, and twice in water. Each sonication lasted for 15 min.

Example 2.3

Signal-on Detection of Complementary Target DNA

A mixture containing 1 µM of Fc-PNA, 1 µM of p-DNA and varying concentrations of t-DNA or nc-DNA was prepared with the hybridization buffer. The mixture was incubated at room temperature for around 5 minutes. Then, 2 µL of the mixture was pipetted onto the chip 70 as shown in FIG. 3A to cover one of the ITO working electrodes 34, the Pt counter electrode 35 and the Pt pseudo-reference electrode 33 and DPV measurement was performed immediately.

Example 2.4

Susceptibility of Signal-Off and Signal-On DNA Detection to False Positive

To compare the susceptibility of signal-off and signal-on DNA detection to false positive results, BSA was used as an interfering substance. For the signal-off DNA detection, the p-DNA was used as the target DNA as half of it was complementary to the Fc-PNA. 1 µM of Fc-PNA was mixed with 0.8 µM of p-DNA or 1 µg/µL BSA and DPV scans were performed. For the signal-on DNA detection, 1 µM of Fc-PNA and 1 µM of p-DNA was mixed with 0.8 µM of t-DNA or 1 µg/µL BSA and DPV scans were performed.

Example 2.5

Chronoamperometry Measurement

A mixture containing 1 µM of Fc-PNA and 1 µM of p-DNA was prepared with the hybridization buffer. 2 µL of the mixture was pipetted onto the chip 70 as shown in FIG. 3A to cover one of the ITO working electrodes 34, the Pt counter electrode 35 and the Pt pseudo-reference electrode 33. Then chronoamperometry measurement was conducted with an applied potential of +0.2 V (vs. Pt). 2 µL of 1 µM t-DNA or nc-DNA was added to the mixture on the chip 70 at a certain point during the chronoamperometry measurement.

Example 2.6

Results

The results shown in 2.6.1-2.6.2 are obtained by the experiment process described in Example 2.3 and the results shown in 2.6.4 are obtained by the experiment process described in Example 2.5. The results shown in 2.6.3 are obtained by the experiment process described in Examples 2.3 and 2.4.

2.6.1 Signal-On Sequence-Specific Detection of Target DNA

In the signal-on DNA detection strategy of the instant invention studied, the competition between the negatively charged target DNA (t-DNA) and a neutrally-charged ferrocene-labeled PNA (Fc-PNA) to hybridize with a probe DNA (p-DNA) determines the charge associated with the Fc, which affects the accessibility of Fc towards the negatively-charged electrode surface. When the 11-bp Fc-PNA probe is hybridized to a complementary sequence in a 20-bp DNA strand (p-DNA), it is difficult for the negatively charged Fc-PNA/p-DNA hybrid to diffuse to the ITO surface, resulting in a much lower electrochemical signal than that produced by free neutral Fc-PNA. In the presence of the 20-bp t-DNA which can form a double-stranded DNA hybrid with p-DNA with a higher melting temperature (69.9° C.) than that of the Fc-PNA/p-DNA hybrid (43.6° C.), hybridization will occur between p-DNA and t-DNA, while the Fc-PNA will be dissociated from p-DNA. As the dissociated Fc-PNA (with a neutral backbone) can freely approach the electrode, a significantly enhanced electrochemical signal of Fc will be observed.

Experimental results are shown in FIG. 9A. With the t-DNA present, a current peak produced by the oxidation of the Fc on the electrode was observed. When either no target DNA was added or the DNA added was non-complementary to p-DNA, no peak of Fc was found in the voltammogram. As the peak appeared only when the target DNA was present, a "signal-on" detection was achieved.

2.6.2 Correlation Between Electrochemical Signal and Target DNA Concentration t-DNA analytes with different concentrations were tested by the signal-on immobilization-free electrochemical DNA detection method. With more t-DNA added, more Fc-PNA will be released from the Fc-PNA/p-DNA hybrids, resulting in a higher electrochemical signal of Fc. As shown in FIG. 9B, a linear relationship between the peak intensity of Fc-PNA and the concentration of the t-DNA could be obtained in the range of 0.1 µM-0.8 µM, equivalent to 0.2 pmol-1.6 pmol.

The detection limit of the signal-on method was determined to be 0.2 μM, which is similar to the detection limit of the aforementioned signal-off method.

In addition, the data presented in FIG. 9B represents the dynamic range of this sensor. For higher concentrations of target DNA, the signal of Fc begins to level off as most of the Fc-PNA has been released from the Fc-PNA/p-DNA hybrids. However, it should be noted that if detection or quantification of higher concentrations of target DNA is needed, the concentration of the Fc-PNA and p-DNA can be increased to provide a dynamic range that covers the desired target DNA concentration.

In one preferred embodiment, interdigitated array (IDA) electrodes can be used to improve the detection sensitivity of the immobilization-free DNA detection. The use of IDA on DNA detection has been reported in Dam V., et al. (Analyst 2007) and Bard A., et al. (Anal. Chem. 1986) to produce a signal amplification factor of up to 60-70. On the closely spaced ultramicroelectrode pairs, the redox species experience multiple redox cycles, resulting in an amplified signal. Due to the diffusion-controlled nature, the IDA signal amplification mechanism would be a perfect match with the immobilization-free DNA detection method of the instant invention. Using IDA electrodes, it is expected that signals of lower concentrations of Fc-PNA can be measured, leading to the detection of lower concentrations of target DNA, that is, higher detection sensitivity.

2.6.3 Comparison of Susceptibility of Signal-Off and Signal-on DNA Detection to False Positive In order to compare the susceptibility of signal-off and signal-on DNA detection to false positive results, BSA was exemplified as an interfering substance. As BSA has a tendency to adsorb on the electrode surface, it will be a barrier for the electron transfer to the solution-electrode interface, resulting in a reduction in the electrochemical signal of Fc. This produces a false positive in signal-off DNA detection, i.e., the signal is reduced even though no target DNA is present. However, in signal-on DNA detection, as there will be no signal when no target DNA is present, the presence of BSA will not lead to any false positive results.

As shown in FIG. 10A, in the signal-off detection the presence of BSA led to signal suppression similar to that caused by the presence of 0.8 μM of target DNA, constituting a false positive. In the signal-on detection of the instant invention as shown in FIG. 10B, no signal was produced when no target DNA was present, regardless of the presence of BSA. Therefore, no false positive was produced in the signal-on DNA detection. The signal-on mode of the immobilization-free DNA detection effectively is proven to prevent the production of false positive results.

2.6.4 Investigation on DNA Hybridization Efficiency

Apart from elimination of the need for a probe immobilization step, another possible advantage offered by the immobilization-free DNA detection strategy of the instant invention is its higher hybridization efficiency, and a reduced assay time. In an immobilization-based DNA detection scheme, a long detection time is expected as the complementary target DNA has to diffuse to the electrode before its hybridization with the immobilized probe. On the other hand, in a signal-on immobilization-free DNA detection, it requires much less time to complete detection because of the fast solution-phase hybridization kinetics for the Fc-PNA/p-DNA and the t-DNA/p-DNA.

As shown in FIG. 11A, electrochemical signal of Fc was insignificant before the introduction of t-DNA. A differential pulse voltammetry (DPV) measurement could be made right after the addition of t-DNA and its signal was similar to the measurement collected 3 minutes after the t-DNA addition. In a chronoamperometry measurement (FIG. 11B), an increase in the signal current was observed immediately after the introduction of t-DNA. These results indicate that the hybridization and dissociation between the Fc-PNA, p-DNA and t-DNA is completed soon after the addition of t-DNA; while in an immobilization-based DNA detection scheme, the required incubation time for hybridization (i.e., diffusion of the free DNA to the immobilized probe surface) could not be ignored.

Example 2.7

Conclusion

In a homogeneous solution phase DNA detection method as described in the instant invention, hybridization between the t-DNA and p-DNA releases the Fc-PNA from the Fc-PNA/p-DNA hybrids, allowing Fc-PNA to freely approach the negatively charged electrode, resulting in a significantly enhanced electrochemical signal of Fc. With a sensitivity similar to that achieved by the aforementioned signal-off immobilization-free electrochemical DNA detection, the signal-on DNA detection of the instant invention effectively eliminates the assay's susceptibility to false positive results and therefore produces detection results that are much more reliable.

The preferred embodiments of the present invention as well as various examples thereof, are thus fully described. Although the description referred to particular embodiments, it will be clear to one skilled in the art that the present invention may be practiced with variation of these specific details. Hence this invention should not be construed as limited to the embodiments set forth herein.

For instance, from the result of the immobilization-free nature of the detection, in particular the study on the DNA hybridization efficiency as described in Example 2.6.4 above, the DNA assay can be completed within one minute. These results suggest that the homogeneous solution phase DNA detection method of the instant invention can be readily combined with PCR for DNA detection and quantification in real time PCR method.

In a normal PCR mixture, the amount of primers added is usually highly excessive to obtain higher amplification efficiency. In an implementation, in order to ensure that the hybridization and extension of the target nucleic acid(s) can produce a detectable difference in the Fc signal, asymmetric PCR protocol can be adopted. Thus, a substantial percentage of the DNA probes will be hybridized with the target nucleic acids, leading to a significant increase of the Fc signal. By the end of the PCR, all of the Fc-PNA probes can be released and the Fc-signal will be reduced to a detectable level.

As the PCR proceeds, more and more target nucleic acids can be produced and hybridize with the DNA probes and such hybridization between the target nucleic acids and the DNA probes could release FC-PNA probes previously bound to the DNA probes. The released FC-PNA probes can then be freely diffused to the electrode to produce a signal intensity change(s) when subjected to an electric potential, and such signal intensity change(s) can correspond to the target nucleic acid(s) produced. The signal intensity change(s) detected and/or measured can further be proportional to the formation of the target nucleic acids in each of the PCR amplification cycles conducted. Also, the electrochemical signal of Fc can increase as the PCR cycles increase and the PCR process can be monitored in real time.

As for the solid phase method, an alternative implementation may be feasible in which the probe, instead of comprising a sequence complementary to the target nuclear acid, may comprise an immobilization unit being operationally coupled to the first primer by sequence complementarity with the first primer. Consequently, the first primer is then associated with or bound to the solid surface through its interaction with the immobilization unit.

REFERENCES (1) Wilhelm, J.; Pingoud, A. *ChemBioChem* 2003, 4, 1120-1128.
(2) Drummond, T. G.; Hill, M. G.; Barton, J. K. *Nature Biotech.* 2003, 21, 1192-1199.
(3) Kerman, K.; Kobayashi, M.; Tamiya, E. *Meas. Sci. Technol.* 2004, 15, R1-R11.
(4) Gooding, J., Justin *Electroanalysis* 2002, 14, 1149-1156.
(5) Wang, J. *Anal. Chim. Acta* 2002, 469, 63-71.
(6) Lai, R. Y.; Lagally, E. T.; Lee, S. H.; Soh, H. T.; Plaxco, K. W.; Heeger, A. J. *PNAS* 2006, 103, 4017-4021.
(7) Lee, T. M. H.; Hsing, I. M. *Anal. Chem.* 2002, 74, 5057-5062.
(8) Lee, T. M. H.; Carles, M. C.; Hsing, I. M. *Lab Chip* 2003, 3, 100-105.
(9) Liu, R. H.; Yang, J.; Lenigk, R.; Bonanno, J.; Grodzinski, P. *Anal. Chem.* 2004, 76, 1824-1831.
(10) Adessi, C.; Matton, G.; Ayala, G.; Turcatti, G.; Mermod, J. J.; Mayer, P.; Kawashima, E. *Nucleic Acids Res.* 2000, 28, e87.
(11) Carmon, A.; Vision, T. J.; Mitchell, S. E.; Thannhauser, T. W.; Muller, U.; Kresovich, S. *BioTechniques* 2002, 32, 410-420.
(12) Luo, X.; Lee, T.; Hsing, I. *Anal. Chem.* 2008, 80 (19), 7341-7346.
(13) Luo, X.; Hsing, I. *Biosensors and Bioelectronics* 2009, 25, 803-808.
(14) Dam, V. A. T.; Olthuis, W.; van der Berg, A. *Analyst* 2007, 132, 365.
(15) Bard, A. J.; Crayston, J. A.; Kittlesen, T. V. Shea; Wrighton M. S. *Anal. Chem.* 1986, 58, 2321.
(16) Ahmed, M. U.; Idegami, K.; Chikae, M.; Kerman, K.; Chaumpluk, P.; Yamamura, S.; Tamiya, E. *Analyst* 2007, 132, 431.
(17) Kobayashi, M.; Kusakawa, T.; Saito, M.; Kaji, S.; Oomura, M.; Iwabuchi, S.; Morita, Y.; Hasan, Q.; Tamiya, E.; *Electrochem. Commun.* 2004, 6, 337.
(18) Fang, T. H.; Ramalingam, N.; Dong, X. D.; Ngin, T. S.; Zeng, X.; Kuan, A. T. L.; Huat, E. Y. P.; Gong, H. Q. *Biosens. Bioelectron.* 2009, 24, 2131.
(19) Duwensee, H.; Jacobsen, M.; Flechsig, G. U. *Analyst* 2009, 134, 899.
(20) Kim, K.; Yang, H.; Park, S. H.; Lee, D. S.; Kim, S. J.; Lim, Y. T.; Kim, Y. T. *Chem. Commun.* 2004, 13, 1466.
(21) Liepold, P.; Kratzmüller, T.; Persike, N.; Bandilla, M.; Hinz, M.; Wieder, H.; Hillebrandt, H.; Ferrer, E.; Hartwich, G. *Anal. Bioanal. Chem.* 2008, 391, 1759.
(22) Mir, M.; Lozano-Sanchez, P.; Katakis, I. *Anal. Bioanal. Chem.* 2008, 391, 2145.
(23) Luo, X.; Hsing, I. *Electroanalysis* 2010, 22(23), 2769-2775.

What is claimed is:

1. A solution phase method for electrochemically or electrically detecting target nucleic acid(s), comprising the steps of:
   a. providing a sample comprising:
      i. a first probe(s) having the same electrical polarity as that of an electrode surface such that said first probe(s) is(are) repelled from said electrode surface; and
      ii. a second probe(s) comprising an electrochemically or electrically conductive labeled marker(s) coupled to an electrically neutral molecule(s), said second probe(s) being operatively linked to said first probe(s);
   b. providing said target nucleic acid(s) to said sample wherein said first probe(s) is(are) complementary to at least a portion of said target nucleic acid(s); and
   c. applying an electric potential to said sample and detecting a signal(s) produced by said labeled marker(s);
   wherein when said first probe(s) is(are) hybridized into said target nucleic acid(s), said second probe(s) is(are) released from said first probe(s) and said labeled marker(s) is(are) freely diffused to said electrode surface to produce a signal intensity change(s) when subjected to an electric potential, and such signal intensity change(s) correspond(s) to said target nucleic acid(s) in said sample.

2. The method according to claim 1 further comprising the step of:
   d. quantifying the amount of said target nucleic acid(s) present in said sample by correlating the signal intensity change(s) over time with the amount of said target nucleic acid(s) present.

3. The method according to claim 1 wherein said step (a) further comprises the step of applying an electric potential to said sample.

4. The method according to claim 1 wherein a melting temperature of a hybridized target nucleic acid(s) and first probe(s) is higher than that of the hybridized second probe(s) and first probe(s).

5. The method according to claim 1 wherein said target nucleic acid(s) comprises a longer sequence than that of said second probe(s).

6. The method according to claim 1 wherein said first probe(s) is(are) fully complementary to said target nucleic acid(s).

7. The method according to claim 1 wherein said second probe(s) is(are) complementary to at least a portion of said first probe(s).

8. The method according to claim 1 wherein said labeled marker(s) comprise(s) ferrocene, ferrocene derivatives, or any combination thereof.

9. The method according to claim 1 wherein said electrically neutral molecule(s) comprise(s) a peptide nucleic acid(s).

10. The method according to claim 1 wherein said signal(s) produced by said labeled marker(s) is(are) electric signal(s).

11. The method according to claim 1 wherein said electrode surface is made of a material selected from the group consisting of indium tin oxide, gold, platinum and carbon materials.

12. The method according to claim 1 wherein an electrode(s) comprise(s) interdigitated array electrode(s).

13. The method according to claim 1 wherein said target nucleic acid(s) comprise(s) an electrically negatively charged DNA(s); said first probe(s) comprise(s) an electrically negatively charged DNA(s) and is(are) fully complementary to said target nucleic acid(s); said second probe(s) comprise(s) a ferrocene-labeled peptide nucleic acid(s); and said electrode surface is electrically negatively charged.

14. The method according to claim 1 wherein said target nucleic acid(s) is(are) produced in a polymerase chain reaction (PCR); said method further comprises the step of quantifying the amount of said target nucleic acid(s) produced by correlating the change(s) in signal(s) over time with the formation of said target nucleic acid(s).

* * * * *

SEQUENCE LISTING

<160> NUMBER OF SEQ ID NOS: 7

<210> SEQ ID NO 1
<211> LENGTH: 37
<212> TYPE: DNA
<213> ORGANISM: Artificial
<220> FEATURE:
<223> OTHER INFORMATION: oligonucleotide probe

<400> SEQUENCE: 1
tttttttttt tttttttttt aaggaaacag ctatgac      37

<210> SEQ ID NO 2
<211> LENGTH: 16
<212> TYPE: DNA
<213> ORGANISM: Artificial
<220> FEATURE:
<223> OTHER INFORMATION: forward primer

<400> SEQUENCE: 2
gtaaaacgac ggccag      16

<210> SEQ ID NO 3
<211> LENGTH: 17
<212> TYPE: DNA
<213> ORGANISM: Artificial
<220> FEATURE:
<223> OTHER INFORMATION: reverse primer

<400> SEQUENCE: 3
aaggaaacag ctatgac      17

<210> SEQ ID NO 4

```
<211> LENGTH: 11
<212> TYPE: DNA
<213> ORGANISM: Artificial
<220> FEATURE:
<223> OTHER INFORMATION: Fc-PNA

<400> SEQUENCE: 4
aaccaccacc a                                                          11

<210> SEQ ID NO 5
<211> LENGTH: 20
<212> TYPE: DNA
<213> ORGANISM: Artificial
<220> FEATURE:
<223> OTHER INFORMATION: DNA probe

<400> SEQUENCE: 5
tggtggtggt tctggtggcg                                                 20

<210> SEQ ID NO 6
<211> LENGTH: 20
<212> TYPE: DNA
<213> ORGANISM: Artificial
<220> FEATURE:
<223> OTHER INFORMATION: target DNA

<400> SEQUENCE: 6
cgccaccaga accaccacca                                                 20

<210> SEQ ID NO 7
<211> LENGTH: 19
<212> TYPE: DNA
<213> ORGANISM: Artificial
<220> FEATURE:
<223> OTHER INFORMATION: nc-DNA

<400> SEQUENCE: 7
ctcaacctcc tgtcaatgc                                                  19
```